United States Patent
Iizuka et al.

[11] Patent Number: 5,538,985
[45] Date of Patent: Jul. 23, 1996

[54] PYRROLIDINONE DERIVATIVES

[75] Inventors: Hajime Iizuka; Takahisa Oguchi; Yoji Aoki; Norio Ohto; Kazutoshi Horikomi; Takaichi Miwa; Takeshi Kamioka; Shoji Kawashima, all of Chiba-ken, Japan

[73] Assignee: Mitsui Toatsu Chemicals, Inc., Tokyo, Japan

[21] Appl. No.: 377,236

[22] Filed: Jan. 24, 1995

[30] Foreign Application Priority Data

Jan. 27, 1994 [JP] Japan .................. 6-007383

[51] Int. Cl.⁶ .................. A61K 31/395; C07D 403/02
[52] U.S. Cl. .................. 514/326; 514/183; 514/213; 514/21; 514/422; 540/480; 540/582; 540/602; 546/208; 548/518; 548/119
[58] Field of Search .................. 546/208; 514/326, 514/422, 183, 213, 214; 548/518, 519; 540/480, 582, 602

[56] References Cited

U.S. PATENT DOCUMENTS

| | | | |
|---|---|---|---|
| 3,717,634 | 2/1973 | Wu et al. | 260/256.4 N |
| 4,423,049 | 12/1983 | Temple, Jr. | 424/251 |
| 4,524,206 | 6/1985 | New et al. | 544/230 |
| 4,668,687 | 5/1987 | Yevich et al. | 514/252 |
| 4,767,759 | 8/1988 | Weber et al. | 514/235.5 |
| 4,826,843 | 5/1989 | Mattson et al. | 514/252 |
| 4,874,422 | 10/1989 | Woolard | 548/518 |
| 4,960,457 | 10/1990 | Woolard | 548/543 |
| 4,963,678 | 10/1990 | Madding et al. | 544/335 |

FOREIGN PATENT DOCUMENTS

| | | |
|---|---|---|
| 136658 | 4/1985 | European Pat. Off. . |
| 2696744 | 4/1994 | France . |
| 1522869 | 8/1978 | United Kingdom . |
| 1532055 | 11/1978 | United Kingdom . |

OTHER PUBLICATIONS

CA103:37365u 4-Aminomethyl-... compositions. Weber et al., p. 502, 1985.
CA110: 231430w Preparation... nootropic use, Weber et al., p. 625, 1989.
J. Med. Chem., vol. 27, pp. 684–691, 1984, Butler et al.
Pol. J. Pharmacol., Pharm., vol. 34, pp. 373–382, 1982, Malawska et al.
J. Med. Chem., vol. 36, pp. 3606–3610, 1993, Ding et al.
Jpn. J. Stroke, vol. 8, pp. 1–8, 1986, Koizumi et al.
Multiple Sigma and PCP Receptor Ligands, pp. 341–353, 1992, Vilner et al.

*Primary Examiner*—Joseph K. McKane
*Attorney, Agent, or Firm*—Burns, Doane, Swecker & Mathis

[57] ABSTRACT

Antipsychotics and ischemic cerebral disease therapeutics comprising as an effective ingredient a compound represented by the following formula (1) or (2):

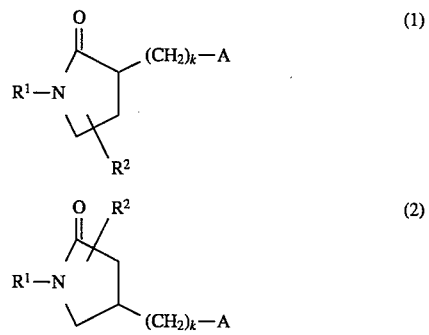

or a salt thereof. These drugs do not induce extrapyramidal side effects.

12 Claims, No Drawings

PYRROLIDINONE DERIVATIVES

BACKGROUND OF THE INVENTION

1. Field of the Invention

This invention relates to novel pyrrolidinone derivatives and also to antipsychotics and ischemic cerebral disease therapeutics containing the derivatives.

2. Description of the Related Art

Schizophrenia occurs at a high rate of one out of every 130 persons and is often developed in adolescence. If a patient is left without adequate treatment, his or her personality progressively deteriorates, resulting in total decay of his or her self-developing functions. Schizophrenia is therefore a serious social problem. As a cause for this disease, certain dopamine dysfunction in the brain has been indicated. The effectiveness of dopamine antagonists such as chlorpromazine and haloperidol as antipsychotics is considered to support the above indication. However, dopamine antagonists are also known to develop at a high rate an extrapyramidal side effect such as acute dystonia, parkinsonism, tardive dyskinesia, thereby presenting another serious problem. In recent years, approaches have been attempted from facets different from the acting mechanisms of conventional drugs. Sigma receptor ligands are considered to be useful for one of such approaches. As "SKF-10047", a sigma receptor agonist, is known to induce psychotic action on men, sigma receptor antagonists are expected to be used as antipsychotics which are not accompanied by extrapyramidal side effects. Rimcazole is known as a drug of this kind, but its affinity and specificity to sigma receptors are still insufficient.

As pyrrolidinone derivatives, compounds represented by the formula (I) are disclosed as herbicides inter alia in U.K. Patent No. 1,522,869 and U.S. Pat. Nos. 4,874,442 and 4,960,457.

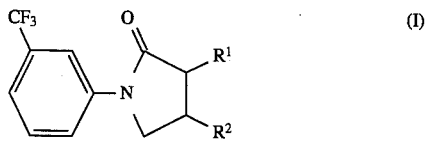

wherein $R^1$ represents —Cl,

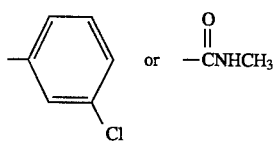

and $R^2$ represents —$CH_2Cl$ or —$C_2H_5$.

For application as pharmaceutical products, compounds represented by the formula (II) are disclosed in U.K. Patent No. 1,532,055 and are reported to have analgesic properties and antidiarrheal properties.

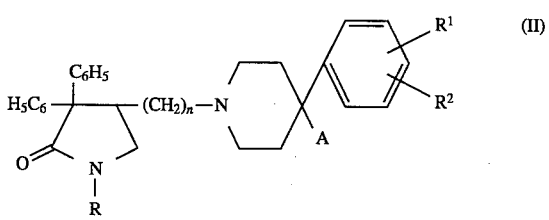

wherein R is selected from the group consisting of H and lower alkyl and benzyl groups; $R^1$ is selected from the group consisting of H, Cl, Br, F, and trifluoromethyl and lower alkoxy groups; $R^2$ is selected from the group consisting of H, Cl, Br and F, A is selected from the group consisting of hydroxy, lower alkylcarbonyloxy and lower alkoxycarbonyl groups, and n stands for an integer of 1, 2 or 3.

For application as other pharmaceutical products, compounds represented by the formula (III) were clinically studied as antidemential drugs. They are disclosed in publications led by Butler et al., "Journal of Medicinal Chemistry", 27, 684–691 (1984).

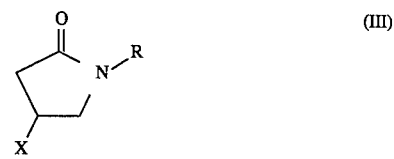

(a) X: H; R: —$CH_2CONH_2$ (piracetam)
(b) X: OH; R: —$CH_2CONH_2$ (oxiracetam)
(c) X: H; R: —$CH_2CONH(CH_2)2N[CH(CH_3)_2]_2$
(d) X: H; R:

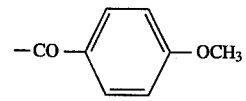

(aniracetam)

Compounds, which have a structure equivalent to that represented by the following formula (IV):

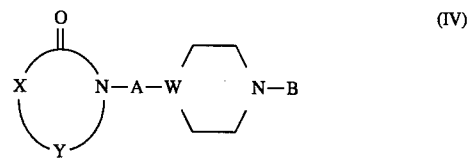

wherein X generally represents a substituted or unsubstituted $C_{2-4}$ alkylene group, Y represents a carbonyl or methylene group, A represents a linking moiety such as an alkylene, alkanoyl or alkyleneamidoalkylene group, W represents a nitrogen atom, and B represents a group having a pyrimidinyl, pyridinyl or benzoisothiazolyl ring, are reported to have antipsychotic, anxiolytic, antiemetic, cognition-enhancing and antidemential activities. They are disclosed in U.S. Pat. Nos. 4,668,687, 3,717,634, 4,423,049 and 4,524,206.

Compounds, which are represented by the following formula (V):

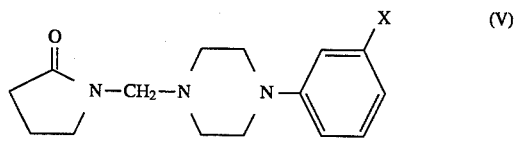

wherein X represents a hydrogen or chlorine atom, are described as exhibiting analgesic properties and at the same time, weak antiinflammatory action in Malawska et al., "Synthesis and Pharmacological Properties of Some 2-Pyrrolidinone Mannich Bases", Polish Journal of Pharmacology, 34, 373–382 (1982). Further, U.S. Pat. No. 4,826,843 to Mattson et al. discloses that compounds of the following formula (VI) have activities to enhance cognition and memory:

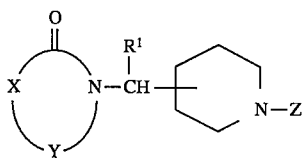

wherein X represents an ethylene chain or a 1,2-benzo ring, Y represents a carbonyl (only when X is a 1,2-benzo ring) or methylene group, $R^1$ represents a hydrogen atom or a lower alkyl group, and Z represents a $R^2,R^3$-disubstituted diazinyl ring selected from pyridazine, pyrimidine and pyrazine rings with $R^2$ and $R^3$ being independently chosen from hydrogen, lower ($C_{1-4}$) alkyl, lower alkoxy, lower alkylthio, cyano, trifluoromethyl, pentafluoroethyl and halogen.

Further, U.S. Pat. No. 4,767,759 discloses that compounds represented by the following formula (VII) have antidemential activities:

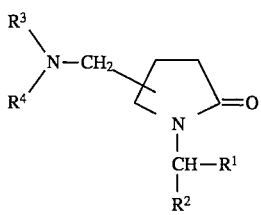

wherein $R^1$ represents a hydrogen atom or a methyl group, $R^2$ represents a pyridyl or phenyl group or a mono or di-substituted phenyl group in which each substituent is a $C_{1-2}$ alkoxy group, fluorine atom, chlorine atom, bromine atom, trifluoromethyl group or $C_{1-4}$ alkyl group, $R^3$ and $R^4$ may be the same or different and represent a hydrogen atom or a $C_{1-2}$ alkyl group or the two groups of $R^3$ and $R^4$ may be coupled together with a nitrogen atom to form a saturated, 5- or 6-membered ring, which may contain O or N as another hetero atom or may have been substituted by methyl groups, or an imidazole ring, and the aminoalkyl group is located at the 4- or 5-position.

In addition, compounds represented by the following formula (VIII):

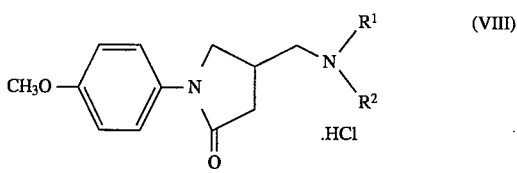

wherein $R^1$ represents $CH_3$ or H and $R^2$ represents $CH_3$ were studied as monoamine oxidase B inhibitors by Silverman et al. [see "Journal of Medicinal Chemistry" 36, 3606–3610 (1993)].

None of the above compounds are however described to have high affinity to sigma receptors and to exhibit antipsychotic action.

SUMMARY OF THE INVENTION

An object of the present invention is to provide a compound having antipsychotic action without developing extrapyramidal side effects.

With a view toward overcoming the above-described problems, the present inventors have proceeded with an extensive investigation on compounds having the pyrrolidinone skeleton. As a result, they have found novel pyrrolidinone derivatives having specific and high affinity to sigma receptors, leading to the completion of the present invention.

The present invention therefore provides a pyrrolidinone derivative represented by the following formula (1) or (2):

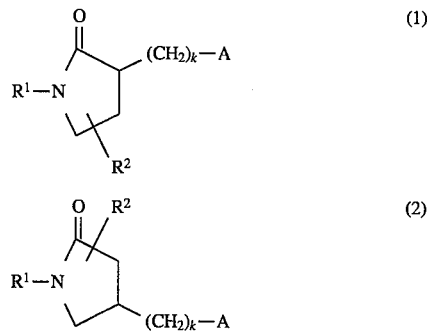

wherein $R^1$ represents a $C_{1-12}$ alkyl group, a group composed of a hydrogenated product of a condensed polycyclic $C_{9-15}$ hydrocarbon, or a substituted or unsubstituted phenyl group, $R^2$ represents a hydrogen atom or a $C_{1-12}$ alkyl group, k stands for an integer of 1 to 3, and A represents a group represented by the following formula (3) or (4):

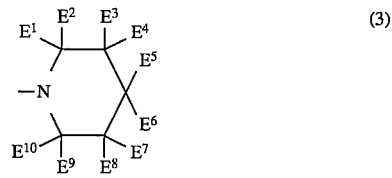

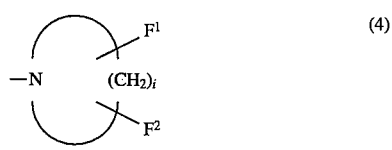

wherein $E^1$, $E^2$, $E^3$, $E^4$, $E^5$, $E^6$, $E^7$, $E^8$, $E^9$ and $E^{10}$ independently represent a hydrogen atom, a hydroxy group, a cyano group, a carbamoyl group, an acetyl group, a halogen atom, a $C_{1-6}$ alkyl group, a $C_{1-6}$ alkoxy group, a $C_{1-4}$ perfluoroalkyl group, a $C_{1-3}$ perfluoroalkyloxy group, a $C_{1-3}$ hydroxyalkyl group, a $C_{1-3}$-alkoxy-substituted $C_{1-3}$ alkyl group, a benzyloxy group or a halogen-substituted benzyloxy group, $F^1$ and $F^2$ independently represent a hydrogen atom, a hydroxy group, a halogen atom, a $C_{1-6}$ alkyl group, a $C_{1-6}$ alkoxy group, a $C_{1-4}$ perfluoroalkyl group or a $C_{1-3}$ perfluoroalkyloxy group, i stands for an integer of 4 or 6 to 9, and when i is 6, $F^1$ and $F^2$ may be coupled together to form an ethylene group; or a salt thereof.

Using as an effective ingredient at least one of such pyrrolidinone derivatives or salts thereof, antipsychotics and ischemic cerebral disease therapeutics can be provided.

Namely, the present invention can provide antipsychotics which do not induce extrapyramidal side effects which have heretofore remained as problems.

Further, the compounds according to the present invention are also expected to be effective as ischemic cerebral disease therapeutics.

DETAILED DESCRIPTION OF THE PREFERRED EMBODIMENTS

In the above formulae (1) and (2), $R^1$ is preferably a linear $C_{1-12}$ alkyl group, a branched $C_{3-12}$ alkyl group, a $C_{3-12}$ alkyl group having a cyclic structure, a group composed of a hydrogenated product of a condensed polycyclic $C_{9-15}$ hydrocarbon, a phenyl group or a substituted phenyl group, and $R^2$ is preferably a hydrogen atom, a linear $C_{1-12}$ alkyl group or a branched $C_{3-12}$ alkyl group.

Preferred as the substituent(s) in the substituted phenyl group represented by $R^1$ are one to three substituents selected from the group consisting of halogen atoms and hydroxy, carbamoyl, sulfamoyl, amino, nitro, cyano, lower alkyl, cycloalkyl, lower alkoxy, lower alkylamino, lower aminoalkyl, lower alkylthio, lower acyl, lower acylamino, lower alkylenedioxy, lower perfluoroalkyl, lower perfluoroalkyloxy, phenyl and benzyloxy groups.

Further, preferred examples of the pyrrolidinone derivative or the salt thereof are those represented by the formula (1) or (2) in which $R^1$ represents a linear $C_{1-5}$ alkyl group, a branched $C_{3-7}$ alkyl group, a $C_{3-10}$ alkyl group having a cyclic structure, a group composed of a hydrogenated product of a condensed polycyclic $C_{9-15}$ hydrocarbon, a phenyl group, or a substituted phenyl group which contains as the substituent(s) thereof one to three substitutes which are each selected from the group consisting of halogen atoms and hydroxy, cyano, linear or branched $C_{1-4}$ alkyl, $C_{3-6}$ cycloalkyl, $C_{1-4}$ alkoxy, $C_{1-4}$ perfluoroalkyl, $C_{1-3}$ perfluoroalkyloxy and phenyl groups; $R_2$ represents a hydrogen atom or a $C_{1-6}$ alkyl group; and A is represented by either the formula (4) described above or the following formula (5):

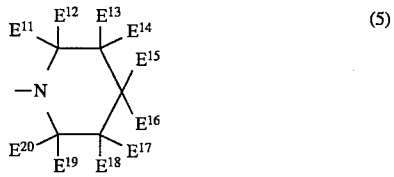

wherein $E^{11}$, $E^{12}$, $E^{13}$, $E^{14}$, $E^{15}$, $E^{16}$, $E^{17}$, $E^{18}$, $E^{19}$ and $E^{20}$ independently represent a hydrogen or halogen atom or a hydroxy, cyano, carbamoyl, acetyl, $C_{1-6}$ alkyl, $C_{1-6}$ alkoxy, $C_{1-4}$ perfluoroalkyl, $C_{1-3}$ perfluoroalkyloxy, benzyloxy or halogen-substituted benzyloxy group.

As described above, the present invention provide antipsychotics and ischemic cerebral disease therapeutics which contain as an effective ingredient one or more of the above compounds.

The present invention will hereinafter be described in detail.

In the definitions for $R^1$ and $R^2$ in the present invention, the term "linear $C_{1-12}$ alkyl group" means, for example, a methyl, ethyl, n-propyl, n-butyl, n-pentyl, n-hexyl, n-octyl or n-dodecyl group. The term "$C_{3-12}$ branched alkyl group" means, for example, an isopropyl, isobutyl, tert-butyl, isopentyl, neopentyl, isohexyl, 3-methylpentyl, 1-methylhexyl, 1-ethylpentyl, 2,3-dimethylbutyl, 1,5-dimethylhexyl, 2-ethylhexyl, 1methylheptyl or t-octyl group. The term "$C_{3-12}$ alkyl group having a cyclic structure" means, for example, a cyclopropyl, cyclobutyl, cyclopentyl, cyclohexyl, cycloheptyl, 2-methylcyclohexyl, 3-methylcyclohexyl, 4-methylcyclohexyl, cyclooctyl, 1-adamantyl, 2-adamantyl or cyclododecyl group.

The term "a group composed of a hydrogenated product of a condensed polycyclic $C_{9-15}$ hydrocarbon" represented by $R^1$ means, for example, a 1-(1,2,3,4-tetrahydro)naphthyl, 5-indanyl, 4-(1,2-cyclopenta-1',3'-dieno)cyclooctenyl or 7-acenaphthenyl group.

A description will now be made in detail of the substituent(s) of the substituted phenyl group represented by $R^1$. The term "halogen atom" means, for example, a fluorine, chlorine, bromine or iodine atom. The term "lower alkyl group" means, for example, a methyl, ethyl, n-propyl, isopropyl, n-pentyl or isopentyl group. The term "cycloalkyl group" means, for example, a cyclopropyl, cyclobutyl, cyclopentyl or cyclohexyl group. The term "lower alkoxy group" means, for example, a methoxy, ethoxy, propoxy, 2-methylethoxy, butoxy, 2-methylpropoxy, pentoxy, 2-methylbutoxy or 2-ethylpropoxy group. The term "lower alkylamino group" means, for example, an N-methylamino, N,N-dimethylamino, N,N-diethylamino, N-methyl-N-ethylamino or N,N-diisopropylamino group. The term "lower aminoalkyl group" means, for example, an aminomethyl, 1-aminoethyl, 2-aminopropyl or 2-aminobutyl group. The term "lower alkylthio group" means, for example, a methylthio, ethylthio, propylthio, 2-methylethylthio or butylthio group. The term "lower acyl group" means, for example, an acetyl, propanoyl or butanoyl group. The term "lower acylamino group" means an acetylamino, propanoylamino or butanoylamino group. The term "lower alkylenedioxy group" means, for example, a methylenedioxy or ethylenedioxy group. The term "lower perfluoroalkyl group" means, for example, a trifluoromethyl or pentafluoroethyl group. The term "lower perfluoroalkyloxy group" means, for example, a trifluoromethoxy or pentafluoroethoxy group.

In the definitions for $E^1$ to $E^{20}$ the terms "halogen atoms", "$C_{1-6}$ alkyl group", "$C_{1-6}$ alkoxy group", "$C_{1-4}$ perfluoroalkyl group" and "$C_{1-3}$ perfluoroalkyloxy group" have the same meanings as defined above. The term "$C_{1-3}$ hydroxyalkyl group" means, for example, a hydroxymethyl or hydroxyethyl group. The term "$C_{1-3}$-alkoxy-substituted $C_{1-3}$ alkyl group" means, for example, a methoxymethyl, methoxyethyl or ethoxymethyl group.

In the definitions for $F^1$ and $F^2$, the terms "halogen atom", "$C_{1-6}$ alkyl group", "$C_{1-6}$ alkoxy group", "$C_{1-4}$ perfluoroalkyl group" and "$C_{1-3}$ perfluoroalkyloxy group" have the same meanings as defined above.

The compounds according to the present invention can be each prepared, for example, in a manner shown below as Reaction Scheme (1).

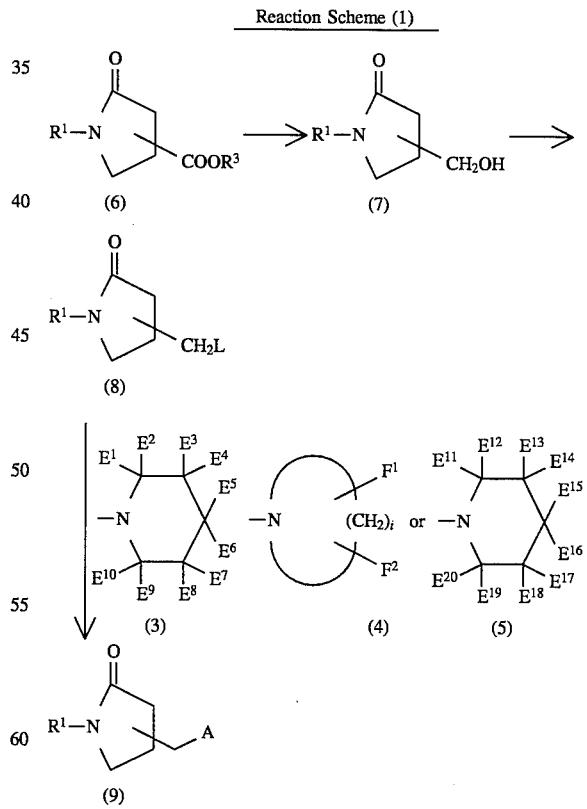

wherein $R^1$, A, $E^1$–$E^{20}$, $F^1$ and $F^2$ have the same meanings as defined above, $R^3$ represents a methyl or ethyl group, and L represents a halogen atom or a tosyloxy or mesyloxy group.

The compound (6) is reduced in an inert solvent to obtain the compound (7). The reaction temperature is −75°–200° C., preferably 0°–100° C., and the reaction time is 1–20 hours, preferably 5–15 hours. Usable examples of the inert solvent include aromatic hydrocarbons such as benzene and toluene; ethers such as diethyl ether, tetrahydrofuran, dioxane, 1,2-dimethoxyethane and ethylene glycol dimethyl ether; halogenated hydrocarbons such as dichloromethane, chloroform and 1,2-dichloroethane; and alcohols such as methanol and ethanol. These inert solvents can be used either singly or in combination. Illustrative examples of usable reducing reagents include aluminum hydride, lithium aluminum hydride, sodium borohydride, a combination of lithium aluminum hydride and aluminum chloride, a combination of sodium borohydride and calcium chloride, and a combination of sodium borohydride and aluminum chloride.

The compound (7) is converted with a thionyl or phosphorus halide to a corresponding halomethyl compound or with a tosyl or mesyl halide to a corresponding tosyl or mesyl ester. It is preferred to conduct this reaction at a temperature of from room temperature to the boiling point of a solvent while using as the solvent an inert organic solvent such as chloroform, dichloromethane, tetrahydrofuran or dimethylformamide. The halomethyl compound or the tosyl or mesyl ester, which is formed as an intermediate, can be isolated or can be reacted further as it is.

When one of these reaction products is reacted with any one of the amines represented by the formulae (3) to (5), the corresponding target compound of the formula (1) or (2) is obtained. This reaction can be carried out in tetrahydrofuran, dioxane, acetonitrile or dimethylformamide. The reaction temperature can be 50°–150° C. but varies depending on the basicity and boiling point of the amine. This reaction can also be conducted in an excess amount of the amine without using any solvent. Usable exemplary bases for the reaction include inorganic bases such as potassium carbonate, sodium carbonate, sodium hydroxide, sodium hydrogencarbonate, sodium amide and sodium hydride; and organic bases such as triethylamine, tripropylamine, pyridine and 1,8-diazabicyclo[5.4.0]undecene-7 (DBU). The above reaction can also be conducted in the presence of an alkali metal iodide compound such as potassium iodide or sodium iodide added as a reaction promoter as needed. Although no particular limitation is imposed on the ratio of the compound represented by the formula (8) to the compound represented by one of the formulae (3) to (5) in the above reaction, the latter can be used generally in an equimolar to excess amount, preferably at a molar ratio of 1–5 relative to the former.

Here, the compound represented by the formula (6) can be synthesized, for example, in the following manner:

Reaction Scheme (2)

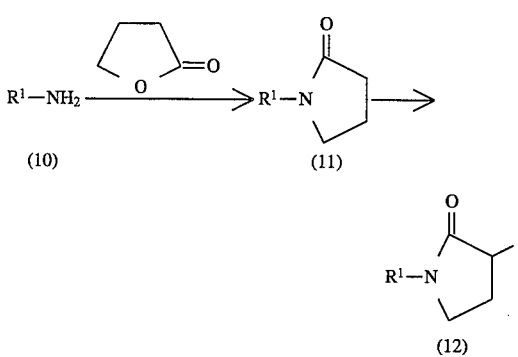

Reaction Scheme (3)

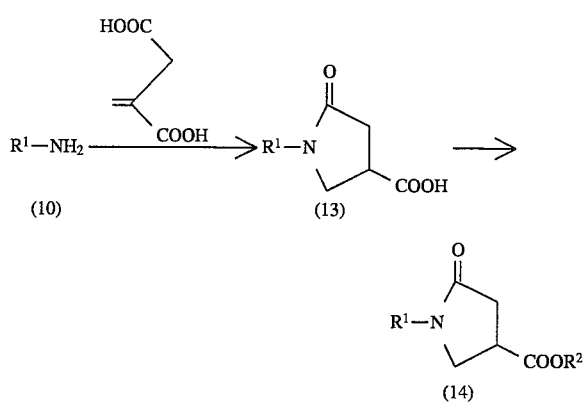

The compound (11) is prepared by subjecting the amine derivative represented by the formula (10) and γ-butyrolactone to dehydrating condensation. This reaction is conducted in a solventless manner under temperature conditions of 50°–250° C., preferably 150°–200° C. for 5–20 hours, preferably 10–15 hours. At this time, an acid catalyst such as hydrochloric acid can be added as needed. An alkoxycarbonyl group is introduced into the resulting compound (11) in the presence of a base in an inert solvent, so that the 3-substituted pyrrolidinone derivative (12) is obtained. The reaction temperature is 30°–200° C., preferably 70°–150° C. and the reaction time is 3–20 hours, preferably 5–15 hours. Illustrative usable examples of the inert solvent include aromatic hydrocarbons such as benzene, toluene and xylene; ethers such as tetrahydrofuran, dioxane, butyl ether and ethylene glycol dimethyl ether; and alcohols such as methanol, ethanol and propanol. Illustrative reagents usable for the introduction of the alkoxycarbonyl group include esters such as dimethyl carbonate, diethyl carbonate, ethyl phosphonoformate and ethyl oxalate. Illustrative examples of the base include inorganic bases such as potassium carbonate, sodium carbonate, sodium amide and sodium hydride; and organic bases such as triethylamine, tripropylamine, pyridine, 1,8-diazabicyclo[5.4.0]undecene-7 (DBU) and potassium tert-butoxide.

The compound (13) can be prepared by subjecting the compound (10) and itaconic acid to dehydrating condensation. This reaction is conducted in a solventless manner under temperature conditions of 50°–250° C., preferably 150°–200° C. for 5–20 hours, preferably 10–15 hours. In this reaction, an acid catalyst such as hydrochloric acid can be added as needed. The compound (13) so obtained is then refluxed in the presence of a catalyst such as sulfuric acid in an alcoholic solvent such as methanol or ethanol, whereby the 4-substituted pyrrolidinone derivative (14) is obtained.

The compound (1) or (2) according to the present invention can easily form a salt with a pharmacologically acceptable ordinary acid. Illustrative examples of the acid include inorganic acids such as sulfuric acid, nitric acid, hydrochloric acid, phosphoric acid and hydrobromic acid; and organic acids such as acetic acid, tartaric acid, fumaric acid, maleic acid, citric acid, benzoic acid, trifluoroacetic acid, methanesulfonic acid, ethanesulfonic acid and p-toluenesulfonic acid. These salts can also be used as effective ingredients in the present invention like the free-form compounds of the formula (1) or (2).

Each derivative of this invention represented by the above formula has one or more asymmetric carbon atoms. Accordingly, the derivative can exist in the form of different stereoisomers or in the form of a mixture of stereoisomers including a racemic form. As a corollary to this, the present invention embraces therein various forms as have been specified above. They are also usable as effective ingredients likewise.

The target compound shown in each of the above reaction schemes can be isolated from the reaction system by a usual isolation means and can then be purified. As these isolation and purification means, it is possible to use, for example, distillation, recrystallization, column chromatography, ion-exchange chromatography, gel chromatography, affinity chromatography, preparative thin-layer chromatography, solvent extraction and/or the like.

Illustrative specific compounds according to the present invention are listed in Table 1. It is however to be noted that the present invention is by no means limited to these examples.

TABLE 1

$$R^1-N\underset{\underset{O}{\parallel}}{\overset{}{\bigcirc}}CH_2-N\underset{}{\bigcirc}-B$$

| No. | $R^1$ | B |
| --- | --- | --- |
| 1 | 4-Cl-C$_6$H$_4$- | $-O-CH(CH_3)_2$ |
| 2 | 4-Cl-C$_6$H$_4$- | $-O-CH_2CH_2CH_2CH_3$ |
| 3 | 4-Cl-C$_6$H$_4$- | $-O-CH_2CH(CH_3)_2$ |
| 4 | 3,4-methylenedioxyphenyl | $-O-CH_3$ |
| 5 | 3,4-methylenedioxyphenyl | $-O-CH_2CH_3$ |
| 6 | 3,4-methylenedioxyphenyl | $-O-CH_2CH_2CH_3$ |
| 7 | 3,4-methylenedioxyphenyl | $-O-CH_2C_6H_5$ |
| 8 | 3,4-methylenedioxyphenyl | $-O-CH(CH_3)_2$ |

TABLE 1-continued
| | | |
|---|---|---|
| 9 | 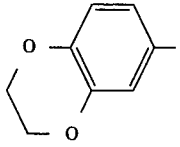 | —O—CH₃ |
| 10 | 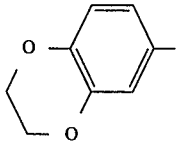 | —O—CH₂CH₃ |
| 11 | 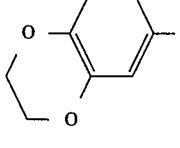 | —O—CH₂CH₂CH₃ |
| 12 | 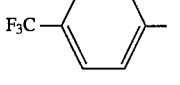 | —O—CH₃ |
| 13 | 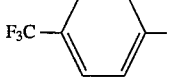 | —O—CH(CH₃)₂ |
| 14 |  | —O—CH₂CH₂CH₃ |
| 15 | 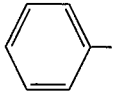 | —O—CH₃ |
| 16 | 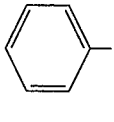 | 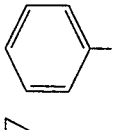 |
| 17 |  | —O—CH(CH₃)₂ |
| 18 |  | —O—CH₃ |
| 19 |  | 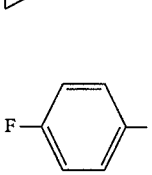 |
| 20 | 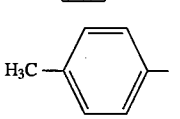 |  |
| 21 | F—⟨⟩— | —O—CH₃ |
| 22 | H₃C—⟨⟩— | —O—CH₃ |
Note: Where LaTeX would normally be used, the subscripts in the R-group column are rendered as: $-O-CH_3$, $-O-CH_2CH_3$, $-O-CH_2CH_2CH_3$, $-O-CH(CH_3)_2$.

TABLE 1-continued

| # | Ar | R |
|---|---|---|
| 23 | 4-(CH₃CH₂)-C₆H₄- | -O-CH₃ |
| 24 | 4-((CH₃)₂CH)-C₆H₄- | -O-CH₃ |
| 25 | 4-((CH₃)₃C)-C₆H₄- | -O-CH₃ |
| 26 | 4-(H₃CO)-C₆H₄- | -O-CH₃ |
| 27 | 4-(F₃CO)-C₆H₄- | -O-CH₃ |
| 28 | 4-(NC)-C₆H₄- | -O-CH₃ |
| 29 | 4-(H₃CCO)-C₆H₄- | -O-CH₃ |
| 30 | 4-(O₂N)-C₆H₄- | -O-CH₃ |
| 31 | 4-(H₂C)-C₆H₄- | -O-CH₃ |
| 32 | 3,4-Cl₂-C₆H₃- | -O-CH₃ |
| 33 | 3,4,5-Cl₃-C₆H₂- | -O-CH₃ |
| 34 | 2,4-Cl₂-C₆H₃- | -O-CH₃ |
| 35 | 2,4,5-Cl₃-C₆H₂- | -O-CH₃ |

TABLE 1-continued

| # | | |
|---|---|---|
| 36 | 2,4,6-trichlorophenyl | —O—CH$_3$ |
| 37 | 2-trifluoromethyl-3-methoxyphenyl (F$_3$C–, H$_3$CO– on phenyl) | —O—CH$_3$ |
| 38 | 3,4-dimethoxyphenyl (H$_3$CO–, H$_3$CO–) | —O—CH$_3$ |
| 39 | H$_3$C— | —O—CH$_3$ |
| 40 | H$_3$CCH$_2$— | —O—CH$_3$ |
| 41 | (CH$_3$)$_2$CH— | —O—CH$_3$ |
| 42 | cyclopropyl-CH$_2$CH$_2$— | —O—CH$_3$ |
| 43 | H$_3$CCH$_2$CH$_2$— | —O—CH$_3$ |
| 44 | H$_3$C(CH$_2$)$_7$CH$_2$— | —O—CH$_3$ |
| 45 | cyclohexyl | —O—CH$_3$ |
| 46 | phenyl-CH$_2$CH$_2$— | —O—CH$_3$ |
| 47 | 4-cyclopentylphenyl | —O—CH$_3$ |
| 48 | 4-cyclopentylphenyl | —O—CH$_2$CH$_3$ |
| 49 | 4-cyclopentylphenyl | —O—CH(CH$_3$)$_2$ |
| 50 | 4-cyclopropylphenyl | —O—CH$_3$ |
| 51 | 4-cyclopropylphenyl | —O—CH$_2$CH$_3$ |
| 52 | 4-cyclopropylphenyl | —O—CH(CH$_3$)$_2$ |

TABLE 1-continued
| No. | | |
|---|---|---|
| 53 | 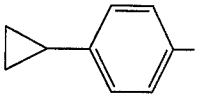 |  |
| 54 | 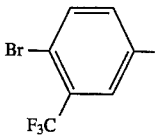 | —O—CH₃ |
| 55 | 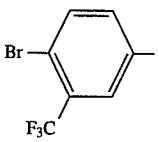 | —O—CH₂CH₃ |
| 56 | 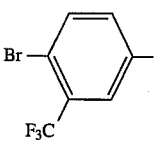 | —O—CH(CH₃)₂ |
| 57 | 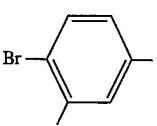 | —O—CH₂CH₃ |
| 58 | 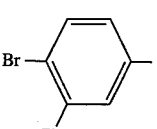 | —O—CH(CH₃)₂ |
| 59 | 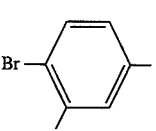 | —O—CH₃ |
| 60 | 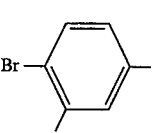 | —O—CH₂CH₃ |
| 61 | 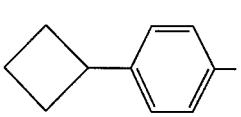 | —O—CH(CH₃)₂ |
| 62 | 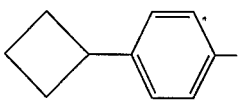 | 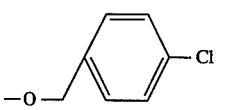 |
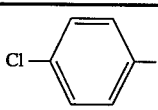
| No. | R¹ | A |
|---|---|---|
| 63 | 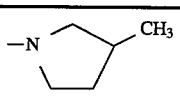 | |

TABLE 1-continued

| # | Ar | NR'R'' |
|---|---|---|
| 64 | 4-Cl-C6H4- | 3-methoxypyrrolidin-1-yl |
| 65 | 4-Cl-C6H4- | 3,4-dimethylpyrrolidin-1-yl |
| 66 | 4-Cl-C6H4- | 3,4-dimethoxypyrrolidin-1-yl |
| 67 | 4-Cl-C6H4- | 4-methylazepan-1-yl |
| 68 | 4-Cl-C6H4- | 4-methoxyazepan-1-yl |
| 69 | 4-Cl-C6H4- | 4,5-dimethylazepan-1-yl |
| 70 | 4-Cl-C6H4- | 4,6-dimethylazepan-1-yl |
| 71 | 4-Cl-C6H4- | 4,5-dimethoxyazepan-1-yl |
| 72 | 4-Cl-C6H4- | 3-hydroxypyrrolidin-1-yl |
| 73 | 4-Cl-C6H4- | 4-hydroxyazepan-1-yl |
| 74 | 4-CF3-C6H4- | 3-methylpyrrolidin-1-yl |
| 75 | 4-CF3-C6H4- | 3-methoxypyrrolidin-1-yl |

TABLE 1-continued
| | | |
|---|---|---|
| 76 | 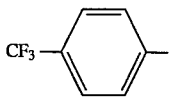 | 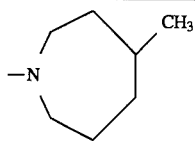 |
| 77 | 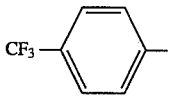 | 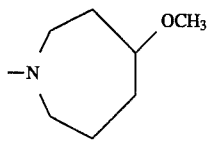 |
| 78 | 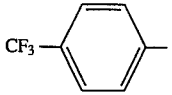 | 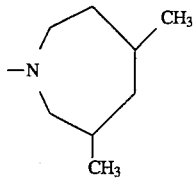 |
| 79 | 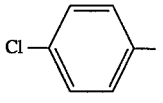 | 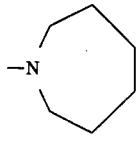 |
| 80 | 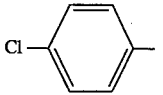 | 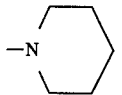 |
| 81 | 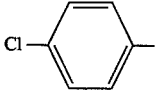 | 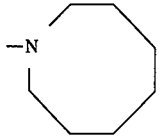 |
| 82 | 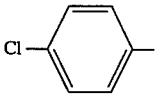 | 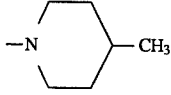 |
| 83 | 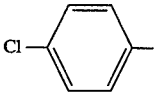 | 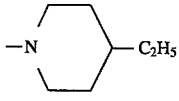 |
| 84 | 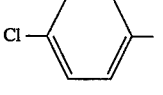 | 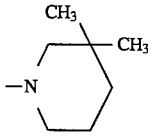 |
| 85 | 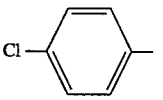 | 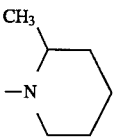 |
| 86 | 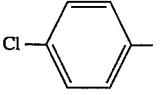 | 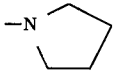 |
| 87 | 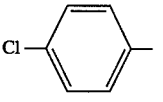 |  |

TABLE 1-continued
| | | |
|---|---|---|
| 88 | 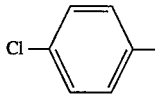 | 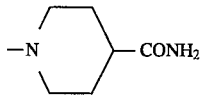 |
| 89 | 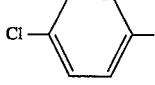 | 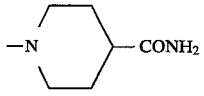 |
| 90 | 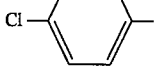 | 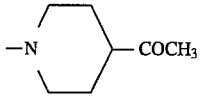 |
| 91 | 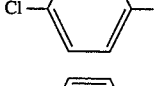 | 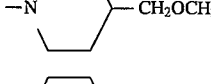 |
| 92 |  | 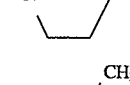 |
| 93 | 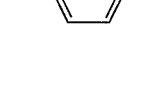 | 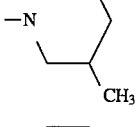 |
| 94 |  | 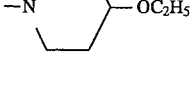 |
| 95 | 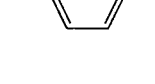 | 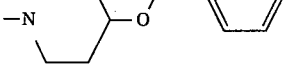 |
| 96 | 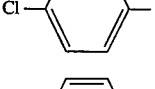 | 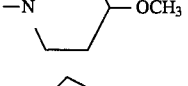 |
| 97 | 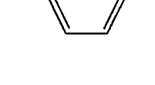 |  |
| 98 | 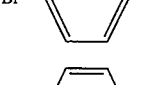 | 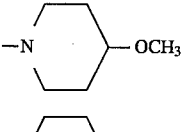 |
| 99 |  | 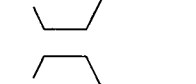 |
| 100 | 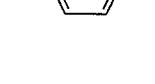 | 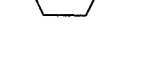 |

TABLE 1-continued
| | | |
|---|---|---|
| 101 | 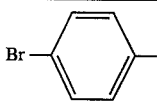 | 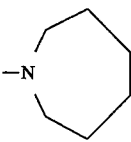 |
| 102 | 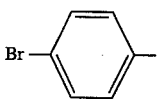 | 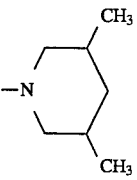 |
| 103 | 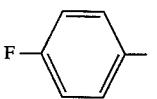 |  |
| 104 | 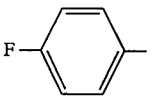 | 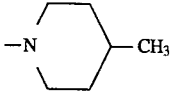 |
| 105 | 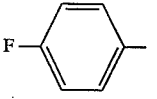 | 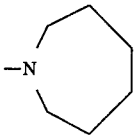 |
| 106 | 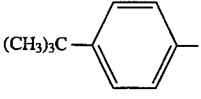 | 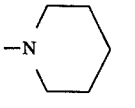 |
| 107 | 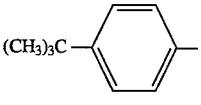 | 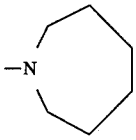 |
| 108 | 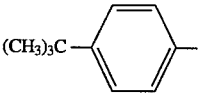 | 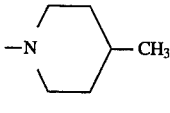 |
| 109 | 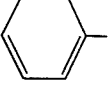 | 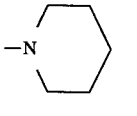 |
| 110 | 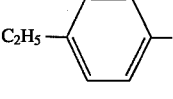 | 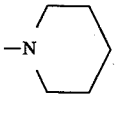 |
| 111 | 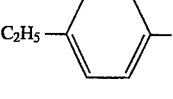 | 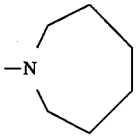 |
| 112 | 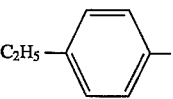 | 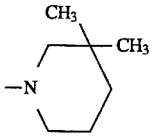 |

TABLE 1-continued
| | | |
|---|---|---|
| 113 | 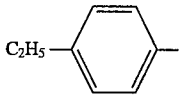 | 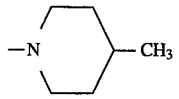 |
| 114 | 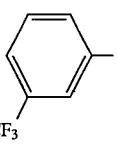 | 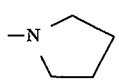 |
| 115 | 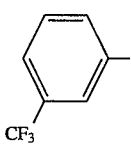 | 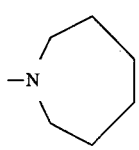 |
| 116 | 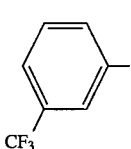 | 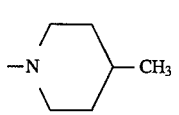 |
| 117 | 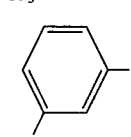 | 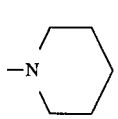 |
| 118 | 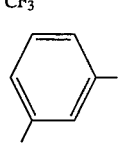 | 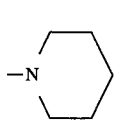 |
| 119 | 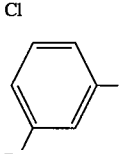 | 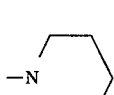 |
| 120 | 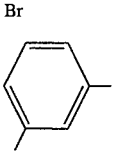 | 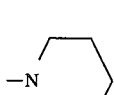 |
| 121 | 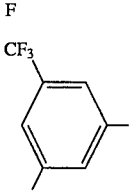 | 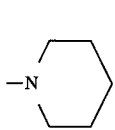 |
| 122 | 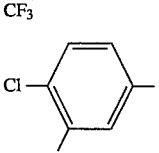 | 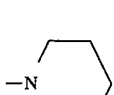 |
| 123 | 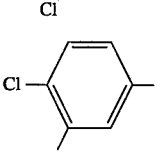 | 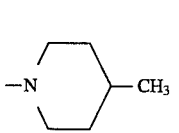 |

TABLE 1-continued
| | | |
|---|---|---|
| 124 | 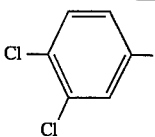 | 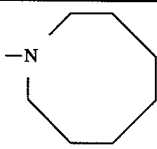 |
| 125 | 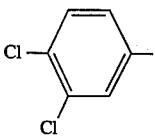 | 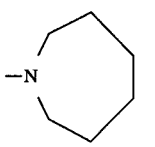 |
| 126 | 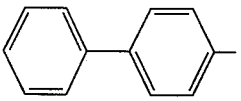 | 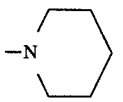 |
| 127 | 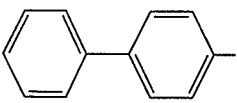 | 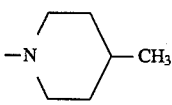 |
| 128 | 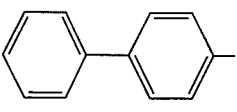 | 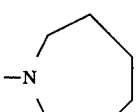 |
| 129 | 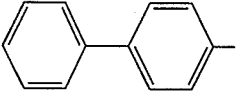 | 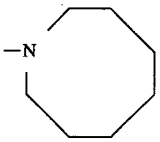 |
| 130 | 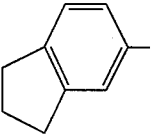 | 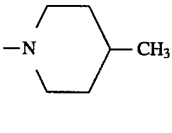 |
| 131 | 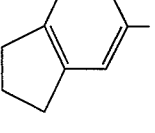 | 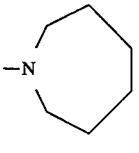 |
| 132 | 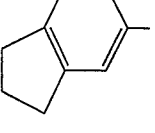 | 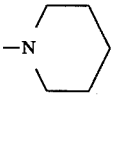 |
| 133 | 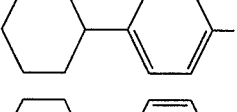 | 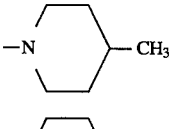 |
| 134 | 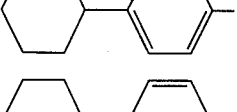 | 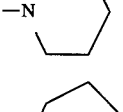 |
| 135 | 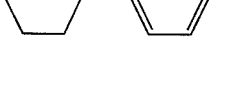 | 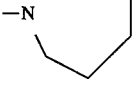 |

TABLE 1-continued
| | | |
|---|---|---|
| 136 | 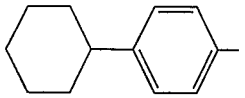 | 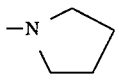 |
| 137 | 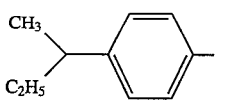 | 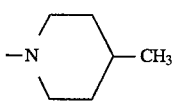 |
| 138 | 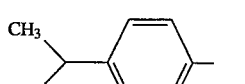 | 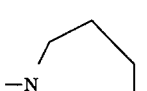 |
| 139 | 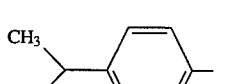 | 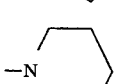 |
| 140 | 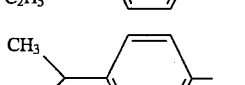 | 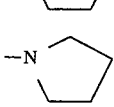 |
| 141 | 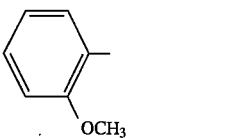 | 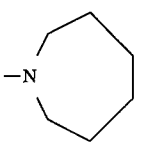 |
| 142 | 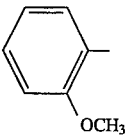 | 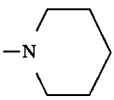 |
| 143 | 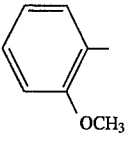 | 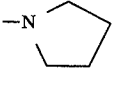 |
| 144 | 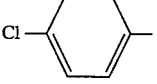 | 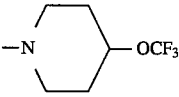 |
| 145 | 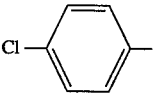 | 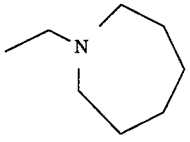 |
| 146 | 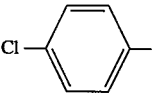 | 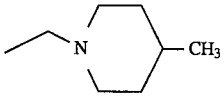 |
| 147 | 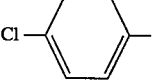 | 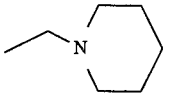 |
| 148 |  | 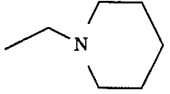 |

TABLE 1-continued

Structure: R¹–N(C=O)–C(R²)(CH₂–A)–CH₂–CH₂ (pyrrolidinone)

| No. | R¹ | R² | A |
|---|---|---|---|
| 149 | phenyl | CH₃ | piperidin-1-yl |
| 150 | 4-Cl-phenyl | CH₃ | 4-methylpiperidin-1-yl |
| 151 | 4-Cl-phenyl | CH₃ | azepan-1-yl (hexamethyleneimino) |
| 152 | 4-Cl-phenyl | C₂H₅ | piperidin-1-yl |
| 153 | 4-C₂H₅-phenyl | CH₃ | 4-methylpiperidin-1-yl |
| 154 | 4-C₂H₅-phenyl | CH₃ | piperidin-1-yl |
| 155 | 3,4-diCl-phenyl | CH₃ | 4-methylpiperidin-1-yl |
| 156 | 3,4-diCl-phenyl | CH₃ | piperidin-1-yl |

Structure: R¹–N(C=O)–CH₂–CH(CH₂–A)–CH₂ (pyrrolidinone)

| No. | R¹ | A |
|---|---|---|
| 157 | phenyl | piperidin-1-yl |
| 158 | 4-CH₃O-phenyl | 4-methylpiperidin-1-yl |
| 159 | 4-CH₃O-phenyl | piperidin-1-yl |

TABLE 1-continued
| | | |
|---|---|---|
| 160 | 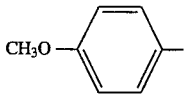 | 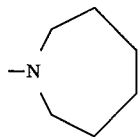 |
| 161 | 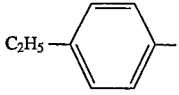 | 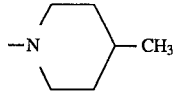 |
| 162 | 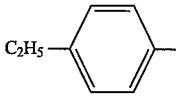 | 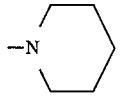 |
| 163 | 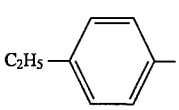 | 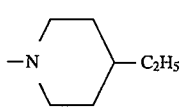 |
| 164 | 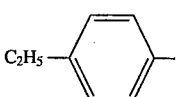 | 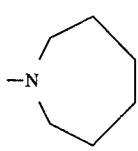 |
| 165 | 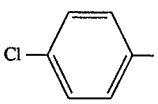 |  |
| 166 | 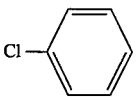 | 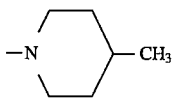 |
| 167 | 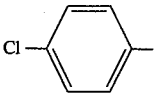 | 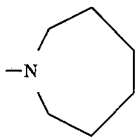 |
| 168 | 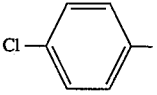 | 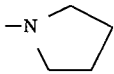 |
| 169 | 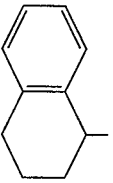 | 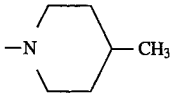 |
| 170 | 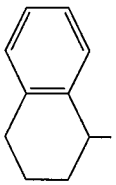 | 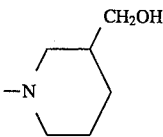 |
| 171 | 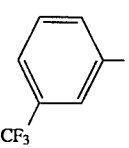 | 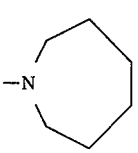 |

TABLE 1-continued

| | | |
|---|---|---|
| 172 | 3-CF₃-C₆H₄- | 4-methylpiperidin-1-yl |
| 173 | 3,4-diCl-C₆H₃- | piperidin-1-yl |
| 174 | 3,4-diCl-C₆H₃- | azepan-1-yl (hexamethyleneimino) |

The compounds obtained as described above are effective as sigma receptor ligands and are used in the forms of general medicinal preparations. These preparations as compositions are formulated by using diluents, carriers or excipients commonly employed in the art, such as fillers, extenders, binders, wetting agents, disintegrators, surfactants and lubricants. As these medicinal preparations, a variety of preparations forms can be chosen depending on the purposes of treatments. Representative examples of preparations include tablets, pills, powders, solutions, suspensions, emulsions, granules, capsules, suppositories, and injections (solutions, suspensions, etc.).

Upon forming tablets, a wide variety of additives conventionally known as vehicles (carriers) in this field of art can be used. Illustrative usable examples of such additives include excipients such as lactose, sucrose, sodium chloride, glucose, urea, starch, calcium carbonate, kaolin, crystalline cellulose and silica; binders such as water, ethanol, propanol, simple syrup, glucose solution, starch solution, gelatin solution, carboxymethylcellulose, shellac, methylcellulose, potassium phosphate and polyvinylpyrrolidone; disintegrators such as dry starch, sodium alginate, agar powder, sodium hydrogencarbonate, calcium carbonate, polyoxyethylene sorbitan fatty acid esters, sodium lauryl sulfate, stearic monoglyceride, starch and lactose; disintegration inhibitors such as sucrose, stearic acid, cacao butter and hydrogenated oil; absorption promoters such as quaternary ammonium bases and sodium lauryl sulfate; moisturizing agents such as glycerin and starch; adsorbents such as starch, lactose, kaolin, bentonite and colloidal silica; and lubricants such as talc, stearate salts, boric acid powder and polyethylene glycol. Further, such tablets can be formed into tablets applied with a conventional coating as needed, for example, sugar coated tablets, gelatin coated tablets, enteric coated tablets, film coated tablets, double layer tablets, or multiple layer tablets.

Upon forming pills, a wide variety of additives conventionally known as vehicles (carriers) in this field of art can be used. Illustrative usable examples of such additives include excipients such as glucose, lactose, starch, cacao butter, hydrogenated vegetable oil, kaolin and talc; binders such as powdered gum arabic, powdered tragacanth and gelatin; and disintegrators such as carmellose calcium and agar.

Upon forming suppositories, a wide variety of additives conventionally known as vehicles in this field of art can be used. Illustrative usable examples of such additives include polyethylene glycol, cacao butter, higher alcohols, esters of higher alcohols, gelatin, and semi-synthetic glyceride.

Capsules are prepared by a conventional method in the art, namely, by mixing one or more of the above compounds as an effective ingredient with one or more of the above-exemplified various vehicles and filling the mixture in hard gelatin capsules, soft capsules or the like.

To prepare as an injection, a solution, emulsion or suspension is sterilized and preferably made isotonic with blood. Upon forming such injections, it is possible to use those commonly employed as diluents in this field of art, for example, water, ethanol, macrogol, propylene glycol, ethoxylated isostearyl alcohol, polyoxylated isostearyl alcohol, and polyoxyethylene sorbitan fatty acid esters. In this case, such medicinal preparations may contain sodium chloride, glucose or glycerin in an amount sufficient to provide isotonic solutions. Further, they can be added with a conventional solubilizing agent, buffering agent, soothing agent or the like.

These medicinal preparations can contain one or more of colorants, preservatives, perfumes, corrigents, sweeteners and other drugs as needed.

No particular limitation is imposed on the amount of each compound to be included as an effective ingredient in such medicinal preparations. The amount of the compound can be chosen from a wide range as needed. In general, however, the effective ingredient can account for about 1–70 wt. % of the composition in each preparation, with about 5–50 wt. % being preferred.

No particular limitation is imposed on the manner of administration of these medicinal preparations. Each medicinal preparation can be administered in a manner suited in view of the kind of its preparation form, the age, sex and other conditions of a patient, and the severity of his or her disease. In the case of tablets, pills, solutions, suspensions, emulsions, granules and capsules, for example, they are orally administered. In the case of injections, they can be intravenously administered by themselves or after mixing them with a conventional fluid replacement such as a glucose or amino acid solution. They can also be administered by themselves intramuscularly, subcutaneously or peritoneally. Suppositories are rectally administered.

The dose of each of these medicinal preparations according to the present invention is suitably chosen depending on the manner of administration, the age, sex and other conditions of a patient, and the severity of his or her disease. In general, however, it is desired to administer it in an amount such that the daily dose of the effective ingredient is about 0.0001–50 mg or so per kg of the body weight. Each preparation in the form of a dosage unit desirably contain an effective ingredient in a range of 0.001–1000 mg.

The present invention will hereinafter be described specifically by the following preparation examples of certain compounds of the present invention and formulation examples of the medical preparations. The present invention will be described in further detail by test examples. It should be borne in mind however that the present invention is not limited to or by the following examples.

EXAMPLE 1

(1-1) Mixed were 372 g (2.916 mol) of p-chloroaniline and 251 g (2.916 mol) of γ-butyrolactone. Heat was absorbed so that the internal temperature dropped to 5° C. To the resulting mixture, 75 ml (0.9 mol) of hydrochloric acid were added, whereby heat was evolved and the internal temperature arose from 5° C. to 30° C. By gradual heating, the resulting mixture started refluxing at an internal temperature of 114° C. The reaction was continued for 9 hours under reflux. Then, the internal temperature was raised gradually. The reaction was conducted at 140° C. for 8 hours. After the internal temperature was cooled to 70° C., the reaction product was dissolved in 2 l of ethyl acetate. The solution so obtained was washed successively with water, an aqueous solution of sodium carbonate and water, dried over magnesium sulfate, and then concentrated to about 1 l to precipitate crystals. The crystals so precipitated were collected by filtration. The filtrate was concentrated to about 200 ml to precipitate further crystals. Both crystals were combined and then washed with ethyl acetate, whereby 347 g of 1-(4-chlorophenyl)-2-pyrrolidinone (No. 1-1) were obtained.

(1-2) With 100 ml of THF, 25 g (0.625 mol) of sodium hydride (60% oil) were mixed, followed by the addition of 34.0 g (0.288 mol) of diethyl carbonate. A solution of 52.0 g (0.266 tool) of the compound (No. 1-1) in 150 ml of THF was added dropwise to the resulting mixture under reflux over about 1.5 hours. After being refluxed for 4.5 hours, the reaction mixture was cooled down and then carefully poured into ice water. The resulting mixture was made weak alkaline with dilute hydrochloric acid and then extracted with 300 ml of ethyl acetate. The extract was washed successively with water, a saturated aqueous solution of sodium bicarbonate (hereinafter called "saturated $NaHCO_3$") and water, dried over magnesium sulfate and then concentrated, whereby an oil was obtained. To the oil so obtained, 200 ml of hexane were added to precipitate crystals. The crystals so precipitated were collected by filtration and then washed with hexane, whereby 60 g of 1-(4-chlorophenyl)-3-ethoxycarbonyl-2-pyrrolidinone (No. 1-2) were obtained.

(1-3) In 150 ml of methanol, 30.0 g (0.112 mol) of the compound (No. 1-2) were dissolved. To the resulting solution, 15 g of anhydrous calcium chloride were added to dissolve the latter in the former. Under ice cooling, 3.9 g (0.103 mol) of sodium borohydride were added to the resulting solution in portions. After disappearance of the sodium borohydride was confirmed, the reaction mixture was concentrated, followed by the addition of water and ethyl acetate. The resulting mixture was made acidic with dilute hydrochloric acid, followed by thorough stirring. The organic layer was separated from the reaction mixture, washed with water, dried and then concentrated. The residue was crystallized from a mixed solvent of hexane and ethyl ether. The crystals so obtained were collected by filtration and washed with the mixed solvent of hexane and ethyl ether, whereby 23.3 g of 1-(4-chlorophenyl)-3-hydroxymethyl-2-pyrrolidinone (No. 1-3) were obtained.

(1-4) In 200 ml of dichloromethane, 23.2 g (0.103 mol) of the compound (No. 1-3) were dissolved, followed by the addition of 12.5 g (0.124 mol) of triethylamine. Under ice cooling, 14.2 g (0.124 mol) of methanesulfonyl chloride were added dropwise to the resultant mixture. The reaction was conducted for 2 hours. The reaction mixture was washed with water, dried over magnesium sulfate and then concentrated to precipitate crystals. The crystals were then washed with ethyl ether, whereby 29.8 g of 1-(4-chlorophenyl)-3-(mesyloxymethyl)-2-pyrrolidinone (No. 1-4) were obtained.

(1-5) In 80 ml of dimethyl cellosolve, 20.0 g (65.8 mmol) of the compound (No. 1-4) were dissolved. To the resulting solution, 18.0 g (0.181 mol) of hexahydro-1H-azepine were added, followed by reaction under reflux for 3.5 hours. The reaction mixture was thereafter concentrated. To the concentrate so obtained, ice water was added to precipitate crystals. The crystals so precipitated were collected by filtration, washed with water and then dissolved in ethyl acetate. The resulting solution was washed with water, dried over magnesium sulfate and then concentrated. During the concentration, a large amount of crystals were precipitated. The crystals were then washed with a mixed solvent of ethyl acetate and hexane, whereby 16.5 g of 1-(4-chlorophenyl)-3-(hexahydro-1H-azepin-1-ylmethyl)-2-pyrrolidinone (No. 1-5) were obtained.

Melting point: 98°–101° C. $^1$H-NMR ($CDCl_3$, δppm); 1.64(8H,br), 2.13(1H,m), 2.33(1H,m), 2.70(6H,m), 3.08(1H,m), 3.77(2H,m), 7.31(2H,d), 7.59(2H,d)

EXAMPLE 2

(2-1) Mixed were 40.0 g (0.247 mol) of 3,4-dichloroaniline and 22 ml of γ-butyrolactone. To the resulting mixture, 7 ml of hydrochloric acid were added, followed by reflux for 5 hours. The reaction mixture was further reacted for 6 hours at a bath temperature of 190°–200° C. After allowed to cool down, the reaction mixture was dissolved in ethyl acetate. The resulting solution was washed successively with water, saturated $NaHCO_3$ and water, dried over magnesium sulfate, treated with activated carbon and then, concentrated. The crystals were washed with ethyl ether, whereby 43.7 g of 1-(3,4-dichlorophenyl)-2-pyrrolidinone (No. 2-1) were obtained.

(2-2) Mixed were 3.0 g (75.0 mmol) of sodium hydride (60% oil) and 20 ml of benzene. To the resulting mixture, 8.4 g (71.2 mmol) of diethyl carbonate were added, followed by the dropwise addition of 40 ml of a benzene solution containing 6.0 g (26.2 mmol) of the compound (No. 2-1) under reflux. Subsequent to reflux for 7 hours, the reaction mixture was allowed to cool down and poured into ice water. The resulting mixture was made acidic with dilute hydrochloric acid, extracted with ethyl acetate, washed successively with water and saturated saline, dried over magnesium sulfate and then concentrated. To the concentrate so obtained, ethyl ether was added to precipitate crystals. The crystals so obtained were collected by filtration and then recrystallized from a mixed solvent of ethyl acetate and ethyl ether, whereby 3.6 g of ethyl 1-(3,4-dichlorophenyl)-2-oxo-3-pyrrolidinecarboxylate (No. 2-2) were obtained.

(2-3) In 50 ml of ethanol, 3.4 g (11.3 mmol) of the compound (No. 2-2) were dissolved. To the resulting solution, 1.6 g of anhydrous calcium chloride were added to dissolve the latter in the former. To the resulting solution, 0.8 g of sodium borohydride was charged in portions. After disappearance of the sodium borohydride was confirmed, the solution was concentrated. Water and ethyl acetate were added to the concentrate. The resulting mixture was made acidic with dilute hydrochloric acid, followed by thorough stirring. The organic layer was thereafter separated, washed with water, dried over magnesium sulfate and then concentrated. The concentrate so obtained was washed with a mixed solvent of hexane and ethyl ether, whereby 2.5 g of 1-(3,4-dichlorophenyl)-hydroxymethyl-2-pyrrolidinone (No. 2-3) were obtained.

(2-4) In 40 ml of dichloromethane, 2.0 g (7.69 mmol) of the compound (No. 2-3) were dissolved. To the resulting solution, 1.3 ml of triethylamine and then, 0.7 ml of methanesulfonyl chloride were added dropwise and they were reacted for one hour. The reaction mixture was washed with water, dried and then concentrated, whereby a mesyl derivative was obtained. Piperidine (7 ml) was added to the mesyl derivative, followed by reflux for one hour. Water and ethyl acetate were added to the reaction product, followed by thorough stirring. The organic layer was thereafter separated, washed with water, dried over magnesium sulfate and then concentrated, whereby an oil was obtained. The oil so obtained was purified by chromatography on a silica gel column (chloroform:methanol=10:1), whereby 1-(3,4-dichlorophenyl)-3-piperidino-methyl-2-pyrrolidinone (free form) was obtained. The resulting compound in the free form was dissolved in methanol. The solution so obtained was made acidic with hydrochloric acid/dioxane, whereby crystals were precipitated. Methanol was added to the crystals so obtained to dissolve the latter in the former, followed by concentration. The crystals so precipitated were collected by filtration and then washed with ethanol, whereby 2.4 g of 1-(3,4-dichlorophenyl)-3-piperidino-methyl-2-pyrrolidinone hydrochloride were obtained.

Melting point: 238°–240° C. $^1$H-NMR (CDCl$_3$, δppm) (free form); 1.55–1.7 (2H,m), 1.85–2.05(4H,m) , 2.1–2.2(1H,m) , 2.7–3.1 (6H,m), 3.2–3.3(2H,m), 3.75–3.9(2H,m) , 7.4–7.5(2H,m), 7.80(1H,d)

EXAMPLE 3

In a similar manner to the steps (2-1, 2-2 and 2-3) of Example 2 except that m-aminobenzotrifluoride was used as a starting material, 1-(3-trifluoromethylphenyl)-3-hydroxymethyl-2-pyrrolidinone (No. 3-1) was synthesized. Using the compound so obtained (No. 3-1; 1.5 g; 5.79 mmol) and 5 ml of hexahydro-1H-azepine, the step (2-4) of Example 2 was repeated likewise, whereby 1.5 g of 1-(3-trifluoromethylphenyl)-3-(hexahydro-1H-azepin-1-ylmethyl)-2-pyrrolidinone hydrochloride were obtained.

Melting point: 162°–163° C.

$^1$H-NMR (CDCl$_3$, δppm) (free form); 1.55–1.7(8H,m), 2.05–2.4(2H,m) , 2.6–2.85(6H,m), 3.0–3.1(1H,m), 3.8–3.9(2H,m), 7.35–7.5(2H,m), 7.75–8.0(2H,m)

EXAMPLE 4

(4-1) Mixed were 36.5 g (280 mmol) of itaconic acid and 35.0 ml (280 mmol) of 4-ethylaniline. They were reacted for 2 hours at 150° C. The reaction mixture was cooled down and the solid so obtained was washed with ethyl ether, whereby 55.6 g of 1-(4-ethylphenyl)-2-oxo-4-pyrrolidinecarboxylic acid (No. 4-1) were obtained.

(4-2) In 500 ml of ethanol, 54.3 g (243 mmol) of the compound (No. 4-1) were suspended. To the resultant suspension, 1.0 ml of concentrated sulfuric acid was added, followed by reflux for 3 hours. The solvent was distilled off and the residue was dissolved in ethyl acetate, followed by washing with saturated NaHCO$_3$. The resultant solution was dried and then concentrated, whereby 60.8 g of 1-(4-ethylphenyl)-4-ethoxycarbonyl-2-pyrrolidinone (No. 4-2) were obtained.

(4-3) In 400 ml of THF, 60.5 g (232 mmol) of the compound (No. 4-2) were dissolved, followed by the addition of 8.7 g (232 mmol) of sodium borohydride. Under reflux, a solution of 20 ml of methanol in 100 ml of THF was added dropwise to the resulting solution over 4 hours. Water was then added to terminate the reaction. The reaction mixture was extracted with ethyl acetate. The extract was then dried and concentrated. The residue was thereafter recrystallized from a mixed solvent of ethyl acetate and 2-propanol, whereby 30.9 g of 1-(4-ethylphenyl)-4-hydroxymethyl-2-pyrrolidinone (No. 4-3) were obtained.

(4-4) In 300 ml of dichloromethane, 27.3 g (124 mmol) of the compound (No. 4-3) were dissolved, followed by the addition of 60 ml of methanesulfonyl chloride and then, 120 me of triethylamine under ice cooling. The reaction was continued for 5 hours at room temperature. To the reaction mixture, saturated NaHCO$_3$ was added, followed by stirring for 6 hours. The organic layer was separated, dried and then concentrated. The residue was purified twice by chromatography on a silica gel column (methanol: chloroform= 0:1–1:40 and ethyl acetate:hexane=1:4–1:0, respectively), whereby 24.6 g of 1-(4-ethylphenyl)-4-mesyloxymethyl-2-pyrrolidinone (No. 4-4) were obtained.

(4-5) To 5 ml of 4-pipecoline, 1.17 g (3.9 retool) of the compound (No. 4-4) were added, followed by reflux for 3 hours. The reaction mixture was poured into water and the resulting mixture was extracted with ethyl acetate. The extract was then dried and concentrated. The residue was purified by chromatography on a silica gel column (chloroform: methanol=40:1). The purified residue was converted into its hydrochloride by using hydrochloric acid/dioxane in methanol, whereby 1.27 g of 1-(4-ethylphenyl)-4-(4-methylpiperidin-1-ylmethyl)-2-pyrrolidinone hydrochloride were obtained.

Melting point: 160°–161° C.

$^1$H-NMR (CDCl$_3$, δppm) (Hydrochloride) 1.06(3H,d,J= 6Hz), 1.29(3H,t,J=7Hz), 1.78(8H,m), 2.7–4.3(8H,m), 7.38 (2H,d,J=9Hz), 7.63(2H,d,J=9Hz)

EXAMPLE 5

To 5 ml of hexahydro-1H-azepine, 0.54 g (1.8 mmol) of the compound (No. 4-4), which had been obtained in Example 4, was added, followed by reflux for 3 hours. The reaction mixture was poured into water and the resulting mixture was extracted with ethyl acetate. The extract was then dried and concentrated. The residue was purified by chromatography on a silica gel column (chloroform:methanol=40:1). The purified residue was converted into its hydrochloride by using hydrochloric acid/dioxane in methanol, whereby 0.23 g of 1-(4-ethylphenyl)-4-(hexahydro-1H-azepin-1-ylmethyl)-2-pyrrolidinone hydrochloride was obtained.

Melting point: 192°–193° C.

$^1$H-NMR (DMSO-d$_6$, δppm): 1.13(3H,t), 1.60(4H,m), 1.84(4H,m), 2.45(6H,m) , 2.70(1H,m), 2.96(1H,m), 3.08(1H,m), 3.24(1H,m), 3.39(1H,m), 3.76(1H,m), 3.98(1H,m), 7.21(2H,d), 7.52(2H,m).

EXAMPLES 6–92

Compounds shown in Table 2 were obtained in a similar manner to Example 1 or Example 4 except that compounds required for the introduction of desired substituents were selected and used.

TABLE 2 (1)

| Example | Structure | m.p. (°C.) | ¹H-NMR (δppm) |
|---|---|---|---|
| 6 | phenyl-N-pyrrolidinone-CH₂-piperidine | Oil | (CDCl₃)1.4–1.7(6H, m)2.3–2.55(7H, m)2.65–2.8(2H, m) 3.65–4.0(2H, m)7.35–7.55(2H, m)7.8–7.95(2H, m) |
| 7 | 4-CH₃O-phenyl-N-pyrrolidinone-CH₂-piperidine | 106–107 | (CDCl₃)1.4–1.7(6H, m)2.25–2.5(7H, m)2.6–2.75(2H, m) 3.80(3H, s)3.6–3.95(2H, m) 6.85–6.95(2H, m)7.45–7.55(2H, m) |
| 8 | 4-CH₃O-phenyl-N-pyrrolidinone-CH₂-(4-CH₃-piperidine) | 211–213 | (CDCl₃)1.07(3H, d)1.79–1.88(2H, m)2.03–2.21(2H, m) 2.35–2.44(1H, m)2.62–2.98(4H, m)3.15–3.28(2H, m) 3.52–3.68(2H, m)3.80(3H, s) 3.97–4.20(2H, m)6.88–6.91(2H, m)7.46–7.51(2H, m) |
| 9 | 3-CF₃-phenyl-N-pyrrolidinone-CH₂-pyrrolidine | 196–197 Hydrochloride | (CDCl₃)1.75–2.2(5H, m) 2.35–3.0(8H, m)3.8–3.9(2H, m)7.35–7.5(2H, m) 7.75–8.05(2H, m) |
| 10 | 3,5-(CF₃)₂-phenyl-N-pyrrolidinone-CH₂-pyrrolidine | 236–238 Hydrochloride | (CDCl₃)1.4–1.5(2H, m)1.5–1.65(4H, m)2.1–2.2(1H, m) 2.35–2.6(6H, m)2.8–2.95(2H, m)3.8–3.9(2H, m)7.63(1H, s)8.17(2H, s) |
| 11 | 3-CF₃-phenyl-N-pyrrolidinone-CH₂-(4-CH₃-piperidine) | 207–208 Hydrochloride | (CDCl₃)0.92(3H, d)1.2–1.7(5H, m)1.95–2.2(3H, m) 2.35–2.6(2H, m)2.8–3.0(4H, m)3.8–3.9(2H, m)7.35–7.95(4H, m) |
| 12 | 3-Cl-phenyl-N-pyrrolidinone-CH₂-piperidine | 78–79 | (CDCl₃)1.35–1.65(6H, m) 2.0–2.1(1H, m)2.3–2.6(6H, m) 2.8–2.9(2H, m)3.75–3.85(2H, m)7.1–7.8(2H, m) |
| 13 | 3-Br-phenyl-N-pyrrolidinone-CH₂-piperidine | 78–79 | (CDCl₃)1.35–1.65(6H, m) 2.0–2.1(1H, m)2.3–2.6(6H, m) 2.8–2.9(2H, m)3.75–3.85(2H, m)7.2–7.3(2H, m) 7.6–7.9(2H, m) |
| 14 | 3-F-phenyl-N-pyrrolidinone-CH₂-piperidine | 86–87 | (CDCl₃)1.35–1.65(6H, m) 2.0–2.1(1H, m)2.3–2.6(6H, m) 2.8–2.9(2H, m)3.75–3.85(2H, m)6.8–6.9(1H, m)7.25–7.4(2H, m)7.5–7.6(1H, m) |

TABLE 2 (1)-continued

| Example | Structure | m.p. (°C.) | ¹H-NMR (δppm) |
|---|---|---|---|
| 15 | (CH₃)₃C-phenyl-N-pyrrolidinone-CH₂-piperidine | 117–118 | (CDCl₃)1.31(9H, m)1.4–1.7 (7H, m)2.0–2.1(1H, m)2.3–2.6(5H, m)2.8–2.9(2H, m) 3.75–3.85(2H, m)7.35–7.6 (4H, m) |
| 16 | phenyl-N-pyrrolidinone-CH₂-piperidine | 108–109 | (CDCl₃)1.2–1.8(6H, m)1.8–3.0(9H, m)3.8–4.0(2H, m) 7.0–7.8(5H, m) |
| 17 | C₂H₅-phenyl-N-pyrrolidinone-CH₂-piperidine | 105–108 | (CDCl₃)1.14–1.82(3H, t, J= 8Hz)1.38–1.82(6H, m)1.82–3.05(11H, m)3.83(2H, dd, J= 9, 6Hz)7.22–7.78(4H, m) |
| 18 | phenyl-N-pyrrolidinone-CH₂CH₂-piperidine | 61–62 | (CDCl₃)1.2–3.0(17H, m)3.6–4.0(2H, m)7.0–8.0(5H, m) |
| 19 | phenyl-N-pyrrolidinone(3-CH₃)-CH₂-piperidine | 213–215 Hydrochloride | (CDCl₃)1.08(3H, s)1.10–1.58(6H, m)1.60–1.90(1H, m) 2.08–2.68(7H, m)3.38–3.84 (2H, m)6.64–7.08(3H, m) 7.20–7.38(2H, m) |
| 20 | 3-CF₃-phenyl-N-pyrrolidinone-CH₂-piperidine | Oil | (CDCl₃)1.2–1.8(6H, m)1.8–3.2(2H, m)3.6–3.9(2H, m) 7.2–7.6(2H, m)7.7–7.8(2H, m) |
| 21 | biphenyl-N-pyrrolidinone-CH₂-piperidine | 175–177 | (CDCl₃)1.20–1.80(6H, m) 1.80–3.00(9H, m)3.68–3.90 (2H, m)7.10–7.70(9H, m) |
| 22 | F-phenyl-N-pyrrolidinone-CH₂-piperidine | 97–99 | (CDCl₃)1.90–3.04(9H, m) 3.60–3.90(6H, m)6.88–7.14 (2H, m)7.40–7.62(2H, m) |
| 23 | Cl-phenyl-N-pyrrolidinone-CH₂-piperidine | 213–214 Hydrochloride | (CDCl₃)1.30–1.76(6H, m) 1.92–3.08(9H, m)3.64–3.90 (2H, m)7.20–7.40(2H, m) 7.40–7.70(2H, m) |
| 24 | CH₃O-phenyl-N-pyrrolidinone-CH₂-piperidine | 104–106 | (CDCl₃)1.30–1.78(6H, m) 2.18–3.00(9H, m)3.62–3.92 (2H, m)3.78(3H, s)6.74–7.00(2H, m)7.36–7.62(2H, m) |

TABLE 2 (1)-continued

| Example | Structure | m.p. (°C.) | ¹H-NMR (δppm) |
|---|---|---|---|
| 25 | 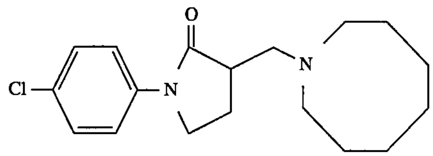 | 174–175 Hydrochloride | (CDCl$_3$)1.56(10H, m)2.23 (1H, m)2.35(1H, m)2.59(5H, m)2.76(1H, m)3.02(1H, m) 3.78(2H, m)7.32(2H, d, J=9Hz)7.59(2H, d, J=9Hz) |
| 26 | 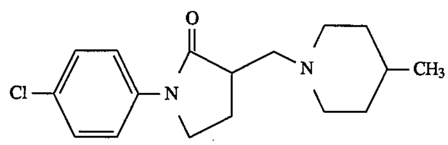 | 223 Hydrochloride | (CDCl$_3$)0.91(3H, d, J=7Hz)1.26 (3H, m)1.59(2H, m)2.04(3H, m)2.35(1H, m)2.54(1H, m)2.86 (4H, m)3.76(2H, m)7.32(2H, d, J=9Hz)7.58(2H, d, J=9Hz) |
| 27 | 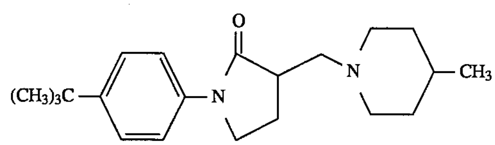 | 252–254 Hydrochloride | (CDCl$_3$)0.91(3H, d)1.31 (9H, s)1.2–1.8(5H, m)1.95– 2.2(3H, m)2.3–2.6(2H, m)2.8– 2.95(4H, m)3.75–3.85(2H, m) 7.35–7.6(4H, m) |
| 28 | 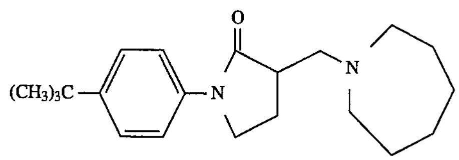 | 250 (dec.) Hydrochloride | (CDCl$_3$)1.31(9H, s)1.55– 1.7(8H, m)2.0–2.4(2H, m) 2.6–2.8(6H, m)3.05–3.15 (1H, m)3.75–3.85(2H, m) 7.35–7.6(4H, m) |
| 29 | 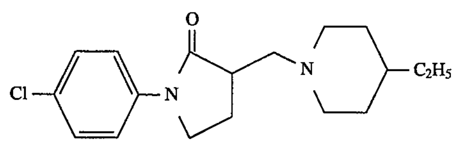 | 129–130 | (CDCl$_3$)0.88(3H, t)1.1–1.3 (5H, m)1.65–1.75(2H, m) 1.9–2.2(3H, m)2.3–2.6(2H, m) 2.8–3.0(4H, m)3.75–3.85 (2H, m)7.25–7.35(2H, m) 7.5–7.65(2H, m) |
| 30 | 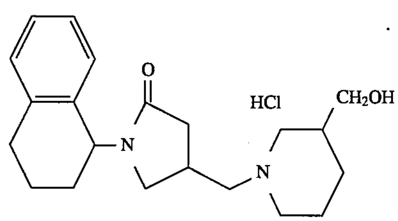 | 208 (dec.) | (DMSO–d$_6$)1.10(1H, m)1.64– 2.04(8H, m)2.30–2.90(6H, m) 3.05–3.40(11H, m)5.17 (1H, m)6.93–7.19(4H, m) |
| 31 | 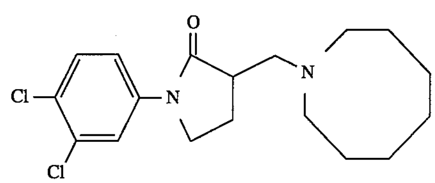 | 128–129 | (CDCl$_3$)1.575(10H, s)2.10 (1H, m)2.52–2.67(4H, m)2.80 1H, m)3.01(1H, dd, J=4, 12Hz) 3.75(2H, m)7.41(1H, d, J=9Hz) 7.56(1H, dd, J=2, 9Hz) 7.80(1H, d, J=3Hz) |
| 32 | 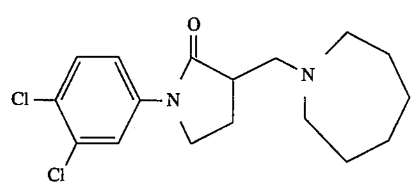 | 124–125 | (CDCl$_3$)1.65(8H, m)2.10 (1H, m)2.41(1H, m)2.66–2.90 (6H, m)3.10(1H, dd, J=4, 12Hz) 3.77(2H, m)7.40(1H, d, J=9Hz) 7.55(1H, dd, J=3, 9Hz) 7.81(1H, d, J=3Hz) |
| 33 | 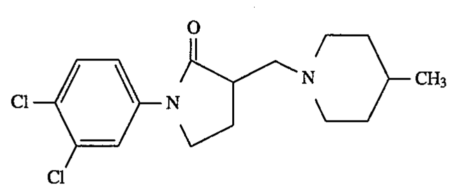 | 126 | (CDCl$_3$)0.92(3H, d, J=7Hz) 1.17–1.38(2H, m)1.63(3H, m) 1.94–2.16(3H, m)2.41(1H, m) 2.54(1H, dd, J=4, 12Hz)2.78– 2.93(4H, m)7.33(1H, d, J= 9Hz)7.55(1H, dd, J=3, 9Hz) 7.81(1H, d, J=2Hz) |

TABLE 2 (1)-continued

| Example | Structure | m.p. (°C.) | ¹H-NMR (δppm) |
|---|---|---|---|
| 34 | 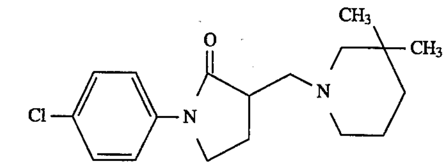 | 116 | (CDCl$_3$)0.92(6H, d, J=2Hz)1.21(2H, t, J=6Hz)1.57(2H, m)1.94–2.53(7H, m)2.70–2.89(2H, m)3.77(2H, m)7.32(2H, m)7.60(2H, m) |
| 35 | 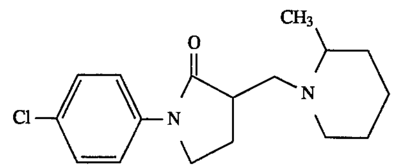 | 225 | |
| 36 | 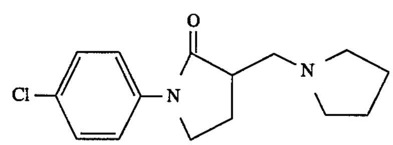 | 216 Hydrochloride | (CDCl$_3$)1.81(4H, br)2.09(1H, m)2.41(1H, m)2.5–2.9(6H, m)3.00(1H, m)3.78(2H, m)7.32(2H, d)7.59(2H, d) |
| 37 | 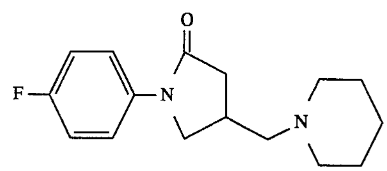 | 195–196 Hydrochloride | (CDCl$_3$)1.56(6H, m)2.39(7H, m)2.69(2H, m)3.64(1H, m)3.89(1H, m)7.05(2H, m)7.58(2H, m) |
| 38 | 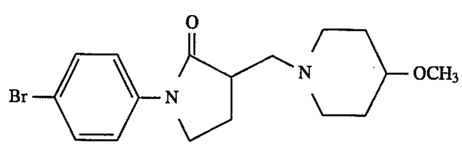 | 127–128 (Hydrochloride: 180–181) | (CDCl$_3$)1.89–2.89(1H, m)3.17–3.24(1H, m)3.340(3H, s)3.74–3.80(2H, m)7.46–7.56(4H, m) |
| 39 | 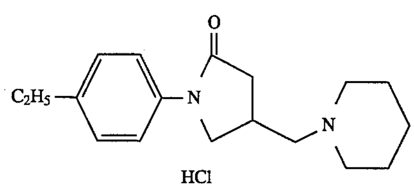 | 205–206 Hydrochloride | (CD$_3$OD)1.22(3H, t)1.56(1H, m)1.90(5H, m)2.58(3H, m)2.86(1H, m)3.04(4H, m)3.31(3H, m)3.58(2H, m)3.75(1H, m)4.10(1H, m)7.23(2H, d)7.47(2H, d) |
| 40 | 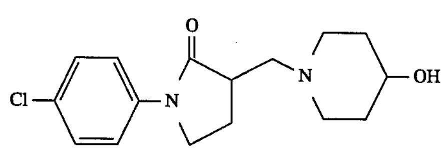 | 119–121 | (CDCl$_3$)1.45–1.8(3H, m)1.8–2.45(6H, m)2.5–2.65(1H, m)2.7–2.95(4H, m)3.65–3.85(3H, m)7.25–7.4(2H, m)7.55–7.75(2H, m) |
| 41 | 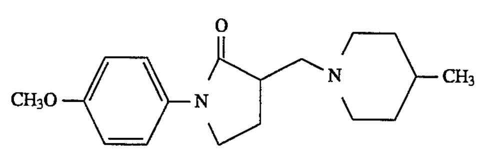 | 101–103 (Hydrochloride: 212–214) | (CDCl$_3$)0.91(3H, d)1.1–1.4(3H, m)1.55–1.65(2H, m)1.9–2.2(3H, m)2.3–2.6(2H, m)2.75–3.0(4H, m)3.75–3.85(5H, m)6.85–6.95(2H, m)7.5–7.6(2H, m) |
| 42 | 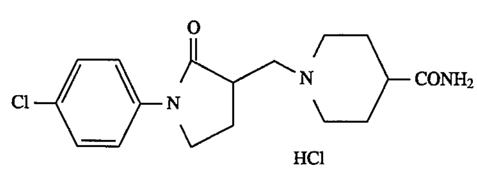 | 247–248 (Free form: 208–209) | (DMSO-d$_6$)1.45–1.7(4H, m)1.8–2.3(5H, m)2.4–2.5(1H, m)2.6–3.0(4H, m)3.75–3.85(2H, m)6.72(1H, s)7.22(1H, s)7.4–7.45(2H, m)7.7–7.75(2H, m) |

TABLE 2 (1)-continued

| Example | Structure | m.p. (°C.) | $^1$H-NMR (δppm) |
|---|---|---|---|
| 43 | 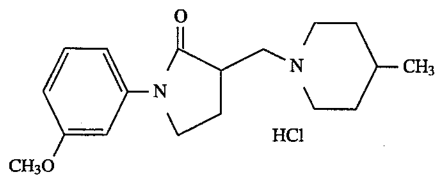 | 208–209 | (DMSO-d$_6$)0.92(3H, d)1.5–2.1(6H, m)2.85–3.6(8H, m)3.75–3.85(2H, m)6.7–6.8(1H, m)7.2–7.4(3H, m) |
| 44 | 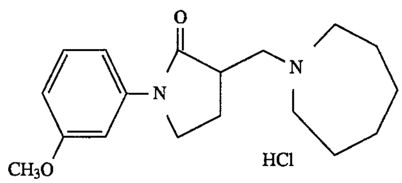 | 196–198 | (DMSO-d$_6$)1.55–2.1(9H, m)3.1–3.6(8H, m)3.76(3H, s)3.75–3.85(2H, m)6.7–6.8(1H, m)7.15–7.4(3H, m) |
| 45 | 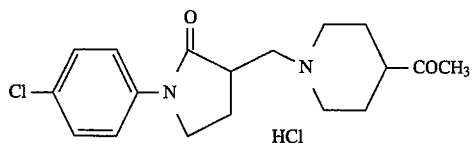 | 221–222 | (CDCl$_3$)1.55–1.7(3H, m)1.8–1.9(2H, m)2.0–2.1(2H, m)2.15(3H, s)2.25–2.4(2H, m)2.55–2.65(1H, m)2.8–3.05(4H, m)3.75–3.85(2H, m)7.3–7.35(2H, m)7.55–7.65(2H, m) |
| 46 | 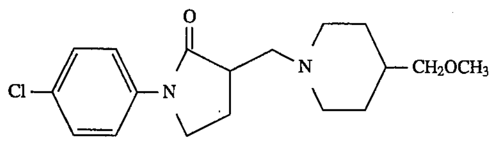 | 126–127 | (CDCl$_3$)1.2–1.35(2H, m)1.55–2.8(3H, m)1.95–2.2 3H, m)2.3–2.4(1H, m)2.5–2.6(1H, m)2.8–3.0(4H, m)3.22(2H, d)3.33(3H, s)3.75–3.85(2H, m)7.25–7.35(2H, m)7.55–7.65(2H, m) |
| 47 | 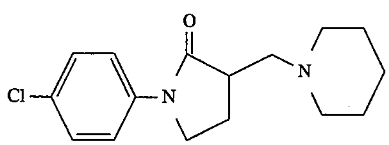 | 138–139 | (CDCl$_3$)1.35–1.65(6H, m)2.0–2.1(1H, m)2.3–2.6(6H, m)2.8–2.9(2H, m)3.7–3.85(2H, m)7.3–7.4(2H, m)7.55–7.65(2H, m) |
| 48 | 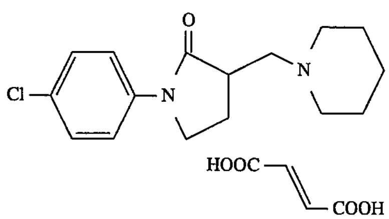 | 165–166 | (CDCl$_3$)1.35–1.65(6H, m)1.85–2.0(1H, m)2.25–2.35(1H, m)2.5–2.75(5H, m)2.8–6.85(2H, s)7.4–7.5(2H, m)7.65–7.75(2H, m) |
| 49 | 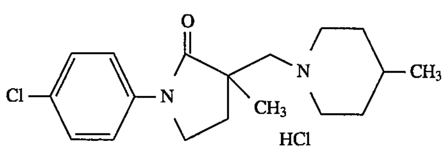 | 201–203 | (DMSO-d$_6$)0.90(3H, d)1.26(3H, s)1.5–1.8(5H, m)2.4–2.5(1H, m)2.9–3.6(6H, m)3.8–3.95(2H, m)7.4–7.5(2H, m)7.7–7.8(2H, m)9.88(1H, s) |
| 50 | 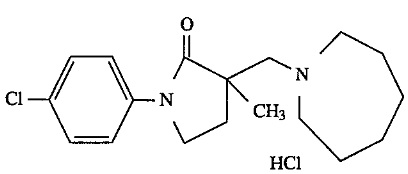 | 229 (dec.) | (DMSO-d$_6$)1.28(3H, s)1.5–1.65(3H, m)1.7–2.0(3H, m)2.05–2.15(1H, m)2.4–2.5(1H, m)3.05–3.55(8H, m)3.75–4.0(2H, m)7.4–7.5(2H, m)7.65–7.75(2H, m)10.38(1H, s) |
| 51 | 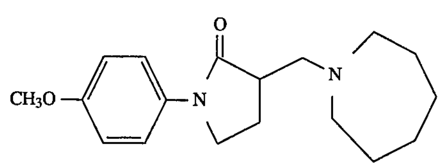 | 72–73 | (CDCl$_3$)1.55–1.7(8H, m)2.05–2.15(1H, m)2.3–2.4(1H, m)2.65–2.8(6H, m)3.05–3.15(1H, m)3.80(3H, s)3.75–3.85(2H, m)6.85–6.95(2H, m)7.45–7.55(2H, m) |

TABLE 2 (1)-continued

| Example | Structure | m.p. (°C.) | ¹H-NMR (δppm) |
|---|---|---|---|
| 52 | 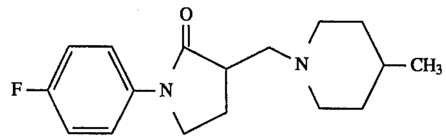 | 106–107 (Hydrochloride: 212–213) | (CDCl₃)0.92(3H, d)1.13–1.39(3H, m)1.58–1.66(2H, m)1.93–2.16(3H, m)2.32–2.38 (1H, m)2.51–2.58(1H, m)2.78–2.93(4H, m)3.75–3.80(2H, m) 7.05(2H, m)7.56–7.61(2H, m) |
| 53 | 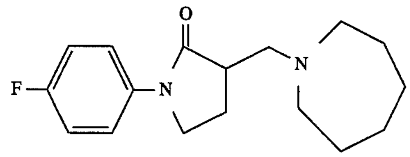 | 80–81 (Hydrochloride: 212–213) | (CDCl₃)1.60(8H, s)2.03–2.16(1H, m)2.28–2.37(1H, m) 2.62–2.83(6H, m)3.08(1H, dd, J=4, 12Hz)3.76–3.81(2H, m) 7.02–7.1(2H, m)7.54–7.62 (2H, m) |
| 54 | 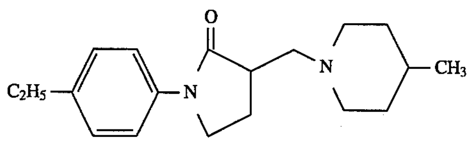 | 102–103 (Hydrochoride: 224–225) | (CDCl₃)0.92(2H, d, J=6Hz) 1.12–1.38(4H, m)1.58–1.65 (2H, m)1.92–2.15(3H, m)2.30–2.40(1H, m)2.50–2.66(3H, m) 2.78–2.94(4H, m)3.75–3.80(2H, m)7.19(2H, d)7.52(2H, d) |
| 55 | 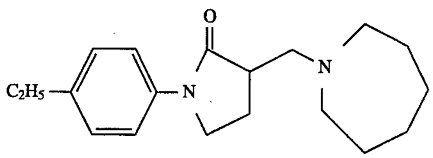 | 56–57 (Hydrochloride: 211–212) | (CDCl₃)1.22(3H, t, J=7Hz) 1.59(8H, s)2.01–2.15(1H, m) 2.24–2.38(1H, m)2.58–2.87 (8H, m)3.09(1H, dd, J=4.12) 3.76–3.81(2H, m)7.19(2H, d, J=9)7.50–7.54(2H, m) |
| 56 | 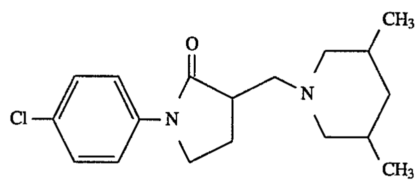 | 119–121 (Hydrochloride: 204–206) | (CDCl₃)0.82–0.95(6H, m) 1.46–1.71(4H, m)1.98–2.91 8H, m)3.71–3.80(2H, m) 7.29–7.35(2H, m)7.57–7.61 (2H, m) |
| 57 | 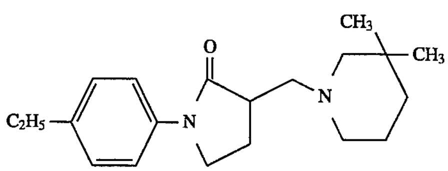 | 73–74 (Hydrochloride: 204–205) | (CDCl₃)0.918(3H, s)0.923 (3H, s)1.19–1.25(3H, m)1.51–1.64(3H, m)1.94–2.87(10H, m)3.72–3.83(2H, m)7.19(2H, d, J=9Hz)7.51–7.54(2H, m) |
| 58 | 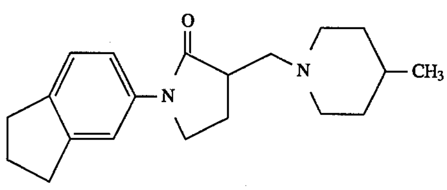 | 99–100 (Hydrochloride: 234–235) | (CDCl₃)0.93(3H, d, J=7Hz) 1.26–1.33(2H, m)1.62–1.63 (2H, m)1.97–2.13(4H, m)2.35–2.60(2H, m)2.85–2.94(8H, m) 3.74–3.84(2H, m)7.18–7.30 (2H, m)7.51(1H, s) |
| 59 | 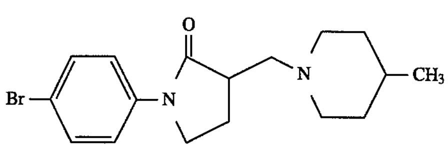 | 132–133 | (CDCl₃)0.92(3H, d, J=6Hz)1.14–1.38(3H, m)1.65–1.66(2H, m)1.93–2.15(3H, m)2.3–2.58 (2H, m)2.77–2.92(4H, m)3.7–3.81(2H, m)7.45–7.57(4H, m) |
| 60 | 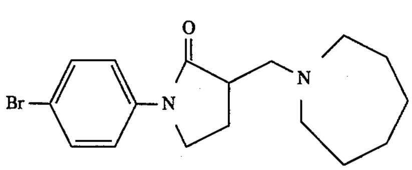 | 101–103 | (CDCl₃)1.58(10H, d, J=5Hz) 2.02–2.16(1H, m)2.28–2.37 (1H, m)2.62–2.84(6H, m)3.07 (1H, dd, J=4, 12Hz)3.71–3.82 (2H, m)7.44–7.58(4H, m) |

TABLE 2 (1)-continued

| Example | Structure | m.p. (°C.) | ¹H-NMR (δppm) |
|---|---|---|---|
| 61 | 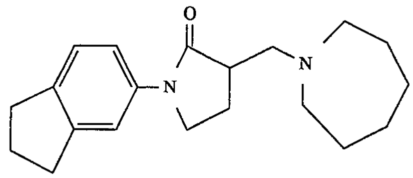 | 67–68 (Hydrochloride: 232–233) | (CDCl$_3$)1.60(8H, s)2.00–2.15(3H, m)2.34–2.35(1H, m)2.54–2.94(10H, m)3.11(1H, dd, J=4, 12Hz)3.76–3.85(2H, m)7.18–7.30(2H, m)7.51(1H, s) |
| 62 | 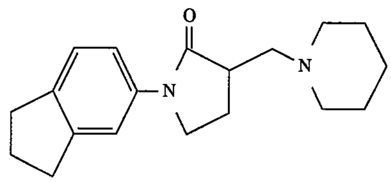 | 79–80 (Hydrochloride: 242–243) | (CDCl$_3$)1.41–1.71(8H, m)1.97–2.12(3H, m)2.28–2.57(6H, m)2.77–2.94(6H, m)3.77(2H, dd, J=3, 8Hz)7.21–7.30(2H, m)7.51(1H, s) |
| 63 | 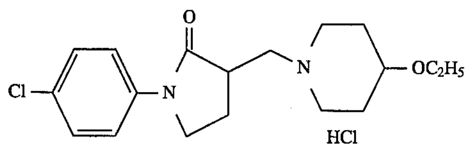 | 122–123 | |
| 64 | 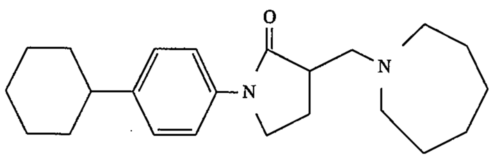 | 124–125 (Hydrochloride: 243–244) | (CDCl$_3$)1.15–2.14(20H, m)2.25–2.80(9H, m)3.08(1H, dd, J=4, 12Hz)3.76–3.82(2H, m)7.14–7.21(2H, m)7.51–7.54(2H, m) |
| 65 | 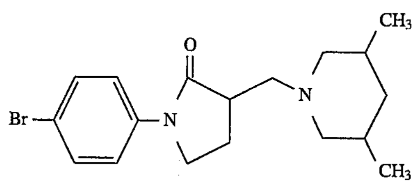 | 128–129 (Hydrochloride: 218–219) | (CDCl$_3$)0.80–0.87(3H, m)0.91–0.95(3H, m)1.46–1.71(6H, m)2.01–2.18(1H, m)2.25–2.88(5H, m)3.76–3.79(2H, m)7.43–7.56(4H, m) |
| 66 | 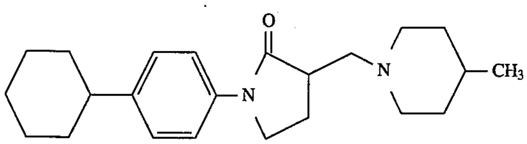 | 242–243 Hydrochloride | (CDCl$_3$)0.91(3H, d, J=7Hz)1.14–1.46(8H, m)1.58–2.57(13H, m)2.75–2.93(4H, m)3.75–3.82(2H, m)7.18–7.20(2H, m)7.51–7.54(2H, m) |
| 67 | 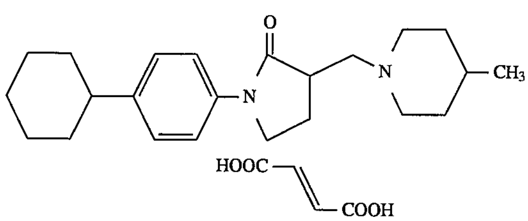 | 185–186 | |
| 68 | 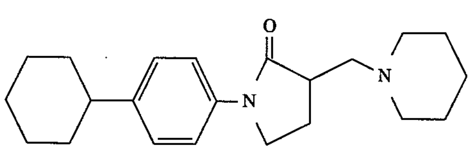 | 148–149 | (CDCl$_3$)1.18–1.56(12H, m)1.72–1.83(4H, m)1.95–2.11(1H, m)2.27–2.56(7H, m)2.76–2.89(2H, m)3.71–3.82(2H, m)7.18–7.21(2H, m)7.50–7.54(2H, m) |
| 69 | 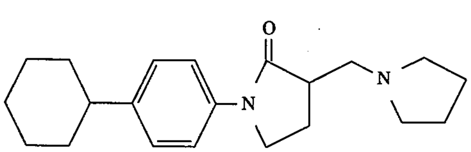 | >250 Hydrochloride | (CDCl$_3$)1.13–1.46(5H, m)1.67–1.86(9H, m)2.03–2.14(8H, m)2.31–2.86(8H, m)2.98(1H, dd, J=4, 11Hz)3.76–3.81(2H, m)7.15–7.22(2H, m)7.50–7.55(2H, m) |

TABLE 2 (1)-continued

| Example | Structure | m.p. (°C.) | ¹H-NMR (δppm) |
|---|---|---|---|
| 70 | 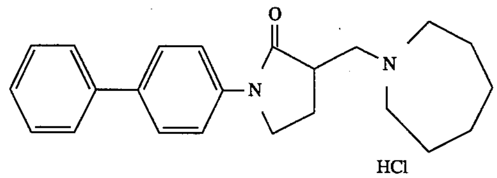 | 246 | (CDCl₃)1.61(8H, m)2.12(1H, m)2.34(1H, m)2.69(6H, m)3.13(1H, m)3.83(2H, m)7.33(1H, m)7.43(2H, m)7.59(4H, m)7.72(2H, m) |
| 71 | 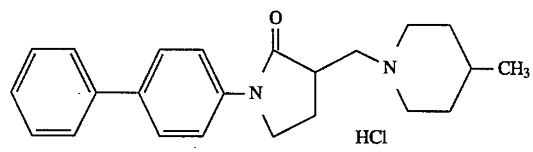 | 250 | (CDCl₃)0.92(3H, d)1.25(2H, m)1.60(3H, m)1.9–2.2(3H, m)2.36(1H, m)2.57(1H, m)2.92(4H, m)3.83(2H, m)(1H, m)7.43(2H, m)7.59(4H, m)7.71(2H, m) |
| 72 | 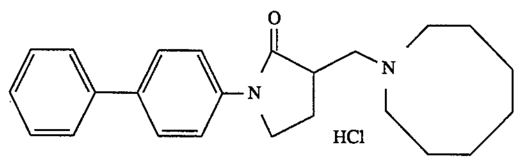 | 156–157 | (CDCl₃)1.73(10H, m)2.18(1H, m)2.55(1H, m)2.80(6H, m)3.02(1H, m)3.88(2H, m)7.32(1H, m)7.44(2H, m)7.60(4H, m)7.70(2H, m) |
| 73 | 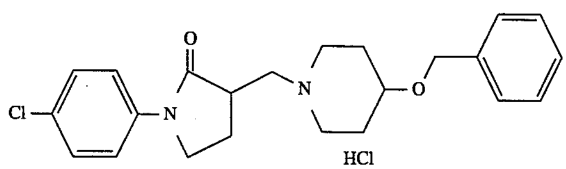 | 200 | (CDCl₃)1.67(4H, m)1.92(1H, m)2.2–2.4(2H, m)2.55(1H, m)2.7–3.0(3H, m)3.41(1H, m)3.78(2H, m)4.55(2H, s)7.30(7H, m)7.58(2H, m) |
| 74 | 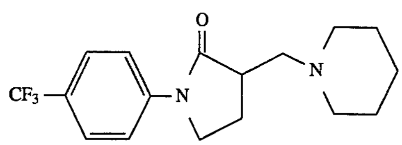 | 115–124 | (CDCl₃)0.85(2H, m)1.58(2H, m)2.09(1H, m)2.54(6H, m)2.85(2H, m)3.82(2H, m)7.61(2H, d)7.77(2H, d) |
| 75 | 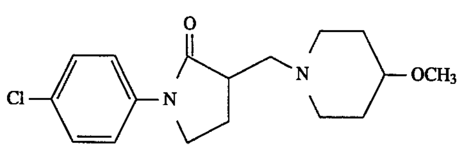 | 103 | (CDCl₃)0.86(2H, m)1.61(2H, m)1.9–2.1(4H, m)2.2–2.5(2H, m)2.62(1H, m)2.7–3.0(3H, m)3.26(1H, m)3.32(3H, s)3.78(2H, m)7.32(2H, d)7.60(2H, d) |
| 76 | 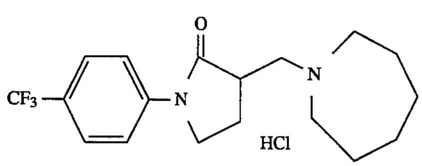 | Amorphous | |
| 77 | 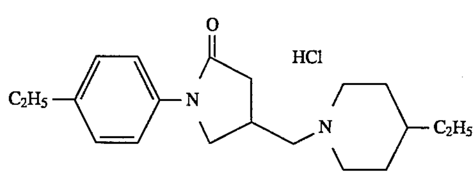 | 207 | (CDCl₃)0.88(3H, t)1.20(7H, m)1.67(3H, m)1.94(2H, m)2.34(3H, m)2.6–3.0(4H, m)3.65(2H, m)3.90(1H, m)7.17(2H, d)7.52(2H, d) |
| 78 | 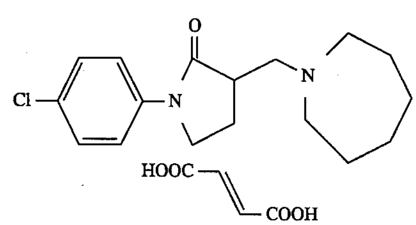 | 147–148 | (DMSO-d₆)1.53(8H, m)1.95(1H, m)2.24(1H, m)2.72(6H, m)2.94(1H, m)3.77(2H, m)6.58(2H, s)7.43(2H, d)7.71(2H, d) |

TABLE 2 (1)-continued

| Example | m.p. (°C.) | ¹H-NMR (δppm) |
|---|---|---|
| 79 | 153–156 | (CDCl₃)1.50(10H, m)1.90(2H, m)2.14(1H, m)2.5–2.7 (4H, m)2.88(2H, m)3.76(2H, m)7.30(2H, d)7.61(2H, d) |
| 80 | 80–81 | (CDCl₃)1.59(8H, m)2.34– 2.76(9H, m)3.65(1H, dd, J= 5, 10Hz)3.89(1H, dd, J= 7, 10Hz)7.29–7.35(2H, m) 7.57–7.63(2H, m) |
| 81 | 100–101 | (CDCl₃)1.59(8H, m)2.34– 2.76(9H, m)3.66(1H, dd, J= 4, 10Hz)3.89(1H, dd, J= 7, 10Hz)7.29–7.35(2H, m) 7.57–7.63(2H, m) |
| 82 | 145–147 | (CDCl₃)1.56–3.02(17H, m) 3.75–3.80(2H, m)6.58(2H, s) 7.41–7.44(2H, m)7.67–7.72 (2H, m) |
| 83 | 51–53 (Hydrochloride: 180–181) | (CDCl₃)0.81(3H, t, J=7Hz) 1.22(3H, d, J=7Hz)1.52–1.63 (10H, m)2.04–2.15(1H, m) 2.26–2.38(1H, m)2.54–2.81 (7H, m)3.09(1H, dd, J=4, 12Hz) 3.76–3.82(2H, m)7.15–7.19 (2H, m)7.52–7.55(2H, m) |
| 84 | 84–85 (Hydrochloride: 225–227) | (CDCl₃)0.81(3H, t, J=7Hz) 1.22(3H, d, J=7Hz)1.41–1.67 (8H, m)2.00–2.12(1H, m)2.31– 2.64(6H, m)2.78–2.90(2H, m) 3.72–3.83(2H, m)7.13–7.18 (2H, m)7.52–7.55(2H, m) |
| 85 | 79–80 (Hydrochloride: 244–245) | (CDCl₃)0.81(3H, t, J=7Hz) 1.22(3H, d, J=7Hz)1.52–1.63 (3H, m)1.79(4H, br)2.00– 2.14(1H, m)2.32–2.86(8H, m) 2.99(1H, dd, J=4, 12Hz)3.77– 3.82(2H, m)7.16–7.19 (2H, m)7.52–7.55(2H, m) |
| 86 | 193–194 | (DMSO-d₆)1.61–2.12(9H, m) 3.16–3.75(10H, m)3.79(3H, 2)6.96–7.36(4H, m)10.33 (1H, s, br) |
| 87 | 220–222 | (DMSO-d₆)1.36–2.14(7H, m) 2.83–3.71(10H, m)3.79(3H, s)6.95–7.36(4H, m)10.34 (1H, s, br) |

TABLE 2 (1)-continued

| Example | Structure | m.p. (°C.) | $^1$H-NMR (δppm) |
|---|---|---|---|
| 88 | 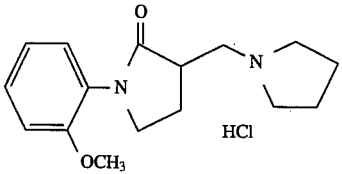 | 178–180 | (DMSO-$d_6$)1.87–2.14(5H, m)3.03–3.75(10H, m)3.79(3H, s)6.95–7.35(4H, m)10.60(1H, s, br) |
| 89 | 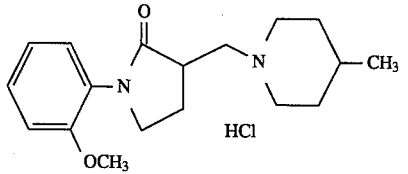 | 216–219 | (DMSO-$d_6$)0.94(3H, d, J=5Hz)1.36–2.16(6H, m)2.57–3.77(10H, m)3.79(3H, s)6.96–7.36(4H, m)10.42(1H, s, br) |
| 90 | 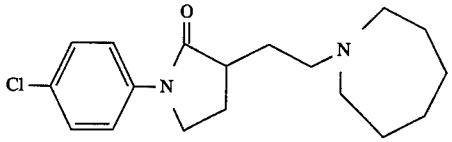 | 125–127 | (CDCl$_3$)1.51–1.90(11H, m)2.11–2.33(1H, m)2.30–2.43(1H, m)2.60–2.75(6H, m)3.76(2H, dd, J=5, 9Hz)7.26–7.33(2H, m)7.57–7.62(2H, m) |
| 91 | 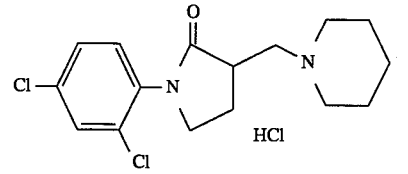 | >230 | (DMSO-$d_6$)1.31–1.44(1H, m)1.68–1.95(5H, m)2.07–2.22(1H, m)2.63–2.76(1H, m)2.83–3.03(1H, m)3.16–3.55(6H, m)3.58–3.72(5H, m)7.50(1H, d, J=9Hz)7.55(1H, dd, J=2.8)7.79(1H, d, J=2)10.47(1H, brS) |
| 92 | 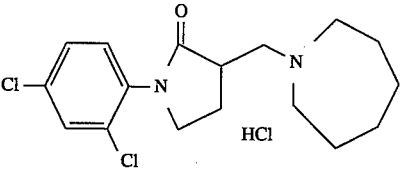 | 180–183 | (DMSO-$d_6$)1.61–1.65(4H, m)1.85(4H, m)2.06–2.21(1H, m)2.58–2.63(1H, m)3.13–3.52(7H, m)3.59–3.76(2H, m)7.49(1H, d, J=9Hz)7.55(1H, dd, J=2.9)7.79(1H, d, J=2)10.42(1H, brS) |

EXAMPLE 93

1-(4-Chlorophenyl)-3-(hexahydro-1H-azepin-1-ylmethyl)-2-pyrrolidinone (3.0 g), which had been prepared in racemic form in Example 1, was subjected to high-performance liquid chromatography for fractionation, whereby 1.4 g of (−) 1-(4-chlorophenyl)-3-(hexahydro-1H-azepin-1-ylmethyl)-2-pyrrolidinone and 1.4 g of (+) 1-(4-chlorophenyl)-3-(hexahydro-1H-azepin-1-ylmethyl)-2-pyrrolidinone were obtained with an optical purity of 99%.

(−) 1-(4-Chlorophenyl)-3-(hexahydro-1H-azepin-1-ylmethyl)-2-pyrrolidinone

Melting point: 218° C. [α]$_D$=−39.4° (0.005 g/ml, H$_2$O, 25° C.)

(+) 1-(4-Chlorophenyl)-3-(hexahydro-1H-azepin-1-ylmethy)-2-pyrrolidinone

Melting point: 219° C. [α]$_D$=−32.8° (0.005 g/ml, H$_2$O, 25° C.)

Conditions for the fractionation were as follows:

HPLC: "LC-10A system" (trade name, manufactured by Shimadzu Corporation)
Column: "CHIRALCEL OD" (trade name; product of Daicel Chemical Industries, Ltd.; 25×2 cm)
Flow rate: 25 ml/min
Mobile phase: hexane:ethanol=100:1

EXAMPLE 94

(Formulation Example 1)

| | |
|---|---|
| 1-(4-chlorophenyl)-3-(hexahydro-1H-azepin-1-ylmethyl)-2-pyrrolidinone hydrochloride | 130 g |
| Citric acid | 1 g |
| Lactose | 35 g |
| Dibasic calcium phosphate | 72 g |
| PLURONIC F-68 | 30 g |
| Sodium laurylsulfate | 20 g |
| Polyvinylpyrrolidone | 14 g |
| Polyethylene glycol ("Carbowax 1500") | 5 g |
| Polyethylene glycol ("Carbowax 6000") | 45 g |
| Corn starch | 33 g |
| Dry sodium stearate | 3 g |
| Dry magnesium stearate | 3 g |
| Ethanol | q.s. |

The compound according to the present invention, i.e., the effective ingredient, the citric acid, the lactose, the dibasic calcium phosphate, the "PLURONIC F-68" and the sodium laurylsulfate were mixed.

The resulting mixture was sifted through a No. 60 screen. Using an ethanol solution containing the polyvinylpyrrolidone, the "Carbowax 1500" and the "Carbowax 6000", the mixture so sifted was wet-granulated. Namely, the powder so-sifted was added with the ethanol in such an amount as needed for the formation of a paste-like mass. The corn starch was added to the paste-like mass, followed by mixing until uniform granules were formed. The granular mixture was caused to pass through a No. 10 screen, placed in a tray, and then dried for 12–15 hours in an oven controlled at 100° C. The granules so dried were sifted through a No. 16 screen, to which dry sodium stearate and dry magnesium stearate were added, followed by mixing. The mixture so obtained was then compressed into cores of a desired shape by a tableting machine.

The cores were treated with a varnish, on which talc was sprinkled to prevent absorption of moisture. Around each core, an undercoat was applied. The varnish was coated again as many times as needed for internal use. To form the resulting tablet into a fully round shape with a smooth surface, an additional undercoat and a smoothcoat were applied further. Color coating was then conducted until a desired coating was obtained. After drying, the tablets so coated were polished into tablets of uniform gloss.

EXAMPLE 95

(Formulation Example 2)

| | |
|---|---|
| 1-(4-Ethylphenyl)-4-(4-methylpiperidino-methyl)-2-piperidinone hydrochloride | 5 g |
| Polyethylene glycol (molecular weight: 4000) | 0.3 g |
| Sodium chloride | 1.0 g |
| Polyoxyethylene-sorbitan monooleate | 0.5 g |
| Sodium metabisulfite | 0.1 g |
| Methylparaben | 0.2 g |
| Distilled water for injection | 10.0 ml |

The methylparaben, sodium metabisulfite and sodium chloride were dissolved under stirring at 80° C. in about a half of the distilled water for injection. The solution so obtained was cooled down to 40° C., followed by the dissolution of the compound according to the present invention, i.e., the effective ingredient and then the polyethylene glycol and polyoxyethylene-sorbitan monooleate in the solution. The remaining distilled water for injection was added to the resulting solution to give the final volume. The mixture so obtained was subjected to bacterial filtration through appropriate a filter paper to sterilize the same, whereby an injection was formulated.

Pharmacological Test 1

By modifying the Vilner et al. method [B. J. Vilner and W. D. Bowen: Mechanisms for Neuromodulation and neuroprotection? in *Multiple Sigma and PCP Receptor Ligands*, pp341 (1992) NPP Books], a radioreceptor assay was conducted with respect to the $\alpha_1$ receptor. A homogenate (10 mg/ml) of the whole brain of a rat except for the cerebellum and medulla was incubated together with each test drug and $^3$H-ligand [5 nM of $^3$H-(+)pentazocine (NEN)] for 2 hours. Brain tissue was filtered under suction through a glass fiber filter paper ("GF/B", trade name; manufactured by Whatman) using a cell harvester ("LL-12", trade name; manufactured by Brandel) and was washed twice, each with 3 ml of a buffer solution. The glass fiber filter paper was placed in a vial, to which 3.5 ml of a scintillator ("ACSII" trade name; product of Amersham International plc) were added. After being left for 10 hours, the amount of $^3$H-ligand bound to the receptor was measured by a liquid scintillation counter. Incidentally, (+)-pentazocine (10 μM) was used for the measurement of a blank.

Binding rates of $^3$H-ligand to the receptor at individual concentrations of each test drug were plotted to draw a graph by assuming that the binding rate without addition of the test drug was 100% and that when the blank substance was added was 0%. A concentration of the test drug, which would give a binding rate of 50%, was then determined and recorded as an $IC_{50}$ value. From the $IC_{50}$ value, the Ki value was determined in accordance with the following formula:

$$Ki = \frac{IC_{50}}{1 + \frac{[^3H\text{-ligand}]}{K_D}}$$

$K_D$ represents the dissociation constant between $^3$H-ligand and the receptor, and was obtained by the Scatchard plotting of the bonding to the receptor when the concentration of $^3$H-ligand was varied. The results are summarized in Table 3.

TABLE 3

| Test drug | Ki(nM) |
|---|---|
| Compound of Example 1 | 2.7 |
| Compound of Example 2 | 2.8 |
| Compound of Example 3 | 3.2 |
| Compound of Example 11 | 2.1 |
| Compound of Example 12 | 4.7 |
| Compound of Example 13 | 1.3 |
| Compound of Example 20 | 3.5 |
| Compound of Example 27 | 2.3 |
| Compound of Example 29 | 3.8 |
| Compound of Example 31 | 1.2 |
| Compound of Example 33 | 7.0 |
| Compound of Example 43 | 3.6 |
| Compound of Example 44 | 5.9 |
| Compound of Example 49 | 3.0 |
| Compound of Example 74 | 4.4 |
| Compound of Example 75 | 8.0 |
| Compound of Example 81 | 9.4 |
| Compound of Example 82 | 2.0 |
| Compound of Example 93 [(−) form] | 1.5 |

Pharmacological Test 2

Using mice, antipsychotic activities were investigated in terms of hyperkinesia induced by methamphetamine. For the experiment, ten 5 weeks-old ddy male mice (NIHON S.L.C K.K.) were used per each group. Immediately after each mouse was peritoneally administered at 10 mg/kg with the corresponding test drug, the mouse was placed in a photocell cage for measurement. The amount of motion was measured for 30 minutes (the first measurement: this was recorded as the action of the test drug for the active movement). Thereafter, the mouse was once taken out of the cage and subcutaneously administered at 1.5 mg/kg with methamphetamine. The mouse was then returned to the same cage and the amount of motion was measured for 30 minutes. An average amount of motion of each group was determined based on the amounts of motion after the administration of methamphetamine (mAMP) as obtained by the second measurement, and the inhibition rate (%) of hyperkinesia was calculated in accordance with the following formula:

Inhibition rate (%) =

$$100 - \frac{\left[\begin{pmatrix}\text{Average amount}\\\text{of motion of}\\\text{the group to}\\\text{which the test}\\\text{drug was}\\\text{administered}\end{pmatrix} - \begin{pmatrix}\text{Average amount}\\\text{of motion of}\\\text{normal group}\end{pmatrix}\right]}{\left[\begin{pmatrix}\text{Average amount}\\\text{of motion of}\\\text{control group}\end{pmatrix} - \begin{pmatrix}\text{Average amount}\\\text{of motion of}\\\text{normal group}\end{pmatrix}\right]} \times 100$$

The group to which the test drug was administered: the test drug+methamphetamine Control group: vehicle+methamphetamine Normal group: vehicle+saline The results are presented in Table 4.

TABLE 4

| Test drug | Inhibition rate of mAMP-induced hyperkinesia (%) |
| --- | --- |
| Compound of Example 1 | 55 |
| Compound of Example 23 | 54 |
| Compound of Example 26 | 56 |
| Compound of Example 33 | 53 |
| Compound of Example 36 | 56 |
| Compound of Example 37 | 62 |
| Compound of Example 39 | 54 |
| Compound of Example 40 | 73 |
| Compound of Example 41 | 53 |
| Compound of Example 45 | 51 |
| Compound of Example 53 | 62 |
| Compound of Example 56 | 76 |
| Compound of Example 64 | 57 |
| Compound of Example 70 | 66 |
| Compound of Example 75 | 66 |
| Compound of Example 81 | 53 |

Pharmacological Test 3

Anticerebral ischemic action was measured following the method proposed by Koizumi et al. [Jun-ichi Koizumi et al, "Experimental studies of ischemic brain edema, I. A new experimental model of cerebral embolism in rats in which recirculation can be introduced in the ischemic area", Jpn. J. Stroke 8: 1–8, 1986)], namely, by the Koizumi's Method MCAo.

One end of a No. 0.8 nylon thread (diameter: 0.148 mm; product of Gosen, Inc.) was brought close to a soldering iron to form a globule of 0.2–0.3 mm in diameter for use as a stopper upon insertion of an artificial embolus. An opposite end of the nylon thread, which was located on a side opposite to the globule, was coated with a waterproof caulking material ("BATHCAULK", trade mark; product of Cemedine Co., Ltd.), thereby forming an artificial embolus of 0.2–0.3 mm in diameter and about 5 mm in length with a nylon thread part (total length composed of the embolus part and the thread part: 16 mm).

Each SD male rat (NIHON S.L.C. K.K.), which was 10–12 weeks old and had a body weight of 330 g or so, was subjected to median neck incision under anesthesia with 1.5% halothane. While paying ultimate attention to the retention of the vagus nerve, the incision was extended to the segment where the left carotid branches. With the segment as the diverging point of the left carotid being held at the center, the common carotid artery and the external carotid artery were separated from the surrounding binding tissue and were ligated with threads, respectively. Further, a thread part was also applied to the origin of the internal carotid artery as a preparation for ligation and fixing which would be conducted subsequent to insertion of the artificial embolus. Subsequently, the common carotid artery was incised and, from the point so incised, the artificial embolus was inserted over a distance of about 15–16 mm toward the internal carotid artery. The artificial embolus was then ligated and fixed at an end thereof proximal to the nylon thread part (i.e., at the globule) to the internal carotid artery by the thread. By the above procedures, the leading end of the artificial embolus extended beyond the segment where the cerebral artery branches and entered the anterior cerebral artery, so that the inlet of the middle cerebral artery was occluded by a main body of the artificial embolus. By the occlusion of the middle cerebral artery, hemiplegia was developed at the forelimb on the opposite side. Using this hemiplegia as an index, rats free of hemiplegia were excluded.

Each drug was either dissolved or suspended in 0.5% CMC/saline and, immediately after the occlusion of the middle cerebral artery, peritoneally administered. A control group was subjected to peritoneal administration of 0.5% CMC/saline immediately after the middle cerebral artery was occluded.

Brain edema was determined based on an increase in the content of water in the cerebral hemisphere on the ischemic side. Two hours after the occlusion of the middle cerebral artery, the animal was decapitated under anesthesia, the brain (which was cut off across the smell brain and cerebellum) was promptly collected, and the wet weights of the left and right cerebral hemispheres were measured. Each hemisphere was dried for 48–72 hours in a hot air drier controlled at 110° C., and its dry weight was measured. The water contents of the respective brain hemispheres were calculated in accordance with the following formula:

Content of removed water (%)=[(wet weight)−(dry weight)]/(wet weight)×100

Percent increase of the content of removed water=[(water content of the left cerebral hemisphere)−(water content of the right cerebral hemisphere)]/(water content of the right cerebral hemisphere)×100

The results are presented in Table 5.

TABLE 5

| Test drug | MCAo Antibrain edematous action (%) measured by the Koizumi's method |
| --- | --- |
| Compound of Example 2 | 16.4 |
| Compound of Example 3 | 16.1 |
| Compound of Example 9 | 15.2 |
| Compound of Example 11 | 23.6 |
| Compound of Example 12 | 10.8 |
| Compound of Example 13 | 15.8 |
| Compound of Example 14 | 13.6 |
| Compound of Example 20 | 22.2 |
| Compound of Example 21 | 22.0 |
| Compound of Example 54 | 33.3 |

A preliminary acute toxicity test was conducted with respect to those showed high effectiveness in the pharmacological tests among the compounds according to the present invention. Using three mice per group, each of such compounds was peritoneally administered at 100 mg/Kg. No case of death was however observed.

What is claimed is:

1. A pyrrolidinone compound represented by the following formula (1) or (2):

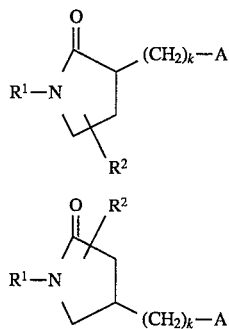

(1)

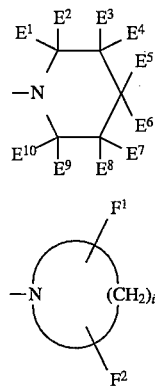

(2)

wherein $R^1$ represents a $C_{1-12}$ alkyl group, a group composed of a hydrogenated product of a $C_{9-15}$ condensed polycyclic hydrocarbon, or a substituted or unsubstituted phenyl group, $R^2$ represents a hydrogen atom or a $C_{1-12}$ alkyl group, k stands for an integer of 1 to 3, and A represents a group represented by the following formula (3) or (4):

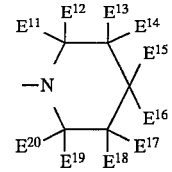

(3)

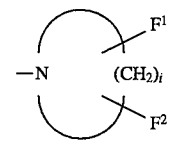

(4)

wherein $E^1$, $E^2$, $E^3$, $E^4$, $E^5$, $E^6$, $E^7$, $E^8$, $E^9$ and $E^{10}$ independently represent a hydrogen atom, a hydroxy group, a cyano group, a carbamoyl group, an acetyl group, a halogen atom, a $C_{1-6}$ alkyl group, a $C_{1-6}$ alkoxy group, a $C_{1-4}$ perfluoroalkyl group, a $C_{1-3}$ perfluoroalkyloxy group, a $C_{1-3}$ hydroxyalkyl group, a $C_{1-3}$-alkoxy-substituted $C_{1-3}$ alkyl group, a benzyloxy group or a halogen-substituted benzyloxy group, $F^1$ and $F^2$ independently represent a hydrogen atom, a hydroxy group, a halogen atom, a $C_{1-6}$ alkyl group, a $C_{1-6}$ alkoxy group, a $C_{1-4}$ perfluoroalkyl group or a $C_{1-3}$ perfluoroalkyloxy group, i stands for an integer of 4 or 6 to 9, and when i is 6, $F^1$ and $F^2$ may be coupled together to form an ethylene group; or a salt thereof.

2. A pyrrolidinone compound or salt according to claim 1, wherein the substituted phenyl group represented by $R^1$ contains as the substituent(s) thereof one to three substituents which are each selected from the group consisting of halogen atoms and hydroxy, carbamoyl, sulfamoyl, amino, nitro, cyano, lower alkyl, cycloalkyl, lower alkoxy, lower alkylamino, lower aminoalkyl, lower alkylthio, lower acyl, lower acylamino, lower alkylenedioxy, lower perfluoroalkyl, lower perfluoroalkyloxy, phenyl and benzyloxy groups.

3. A pyrrolidinone compound or salt according to claim 2, wherein $R^1$ represents a linear $C_{1-5}$ alkyl group, a branched $C_{3-7}$ alkyl group, a $C_{3-10}$ alkyl group having a cyclic structure, a group composed of a hydrogenated product of a condensed polycyclic $C_{9-15}$ hydrocarbon, a phenyl group, or a substituted phenyl group which contains as the substituent(s) thereof one to three substituents which are each selected from the group consisting of halogen atoms and hydroxy, cyano, linear or branched $C_{1-4}$ alkyl, $C_{3-6}$ cycloalkyl, $C_{1-4}$ alkoxy, $C_{1-4}$ perfluoroalkyl, $C_{1-3}$ perfluoroalkyloxy and phenyl groups; $R_2$ represents a hydrogen atom or a $C_{1-6}$ alkyl group; and A represents a group represented by the following formula (5):

(5)

wherein $E^{11}$, $E^{12}$, $E^{13}$, $E^{14}$, $E^{15}$, $E^{16}$, $E^{17}$, $E^{18}$, $E^{19}$ and $E^{20}$ independently represent a hydrogen or halogen atom or a hydroxy, cyano, carbamoyl, acetyl, $C_{1-6}$ alkyl, $C_{1-6}$ alkoxy, $C_{1-4}$ perfluoroalkyl, $C_{1-3}$ perfluoroalkyloxy, benzyloxy or halogen-substituted benzyloxy group.

4. A pyrrolidinone compound or salt according to claim 2, wherein $R^1$ represents a linear $C_{1-5}$ alkyl group, a branched $C_{3-7}$ alkyl group, a $C_{3-10}$ alkyl group having a cyclic structure, a group composed of a hydrogenated product of a condensed polycyclic $C_{9-15}$ hydrocarbon, a phenyl group, or a substituted phenyl group which contains as the substituent(s) thereof one to three substituents which are each selected from the group consisting of halogen atoms and hydroxy, cyano, linear or branched $C_{1-4}$ alkyl, $C_{3-6}$ cycloalkyl, $C_{1-4}$ alkoxy, $C_{1-4}$ perfluoroalkyl, $C_{1-3}$ perfluoroalkyloxy and phenyl groups; $R_2$ represents a hydrogen atom or a $C_{1-6}$ alkyl group; and A represents a group represented by the following formula (4):

(4)

wherein $F^1$ and $F^2$ independently represent a hydrogen atom, a hydroxy group, a halogen atom, a $C_{1-6}$ alkyl group, a $C_{1-6}$ alkoxy group, a $C_{1-4}$ perfluoroalkyl group or a $C_{1-3}$ perfluoroalkyloxy group, and i stands for an integer of 4 or 6 to 9.

5. An antipsychotic composition comprising as an effective ingredient the compound or salt according to claim 4.

6. An ischemic cerebral disease therapeutic composition comprising as an effective ingredient the compound or salt according to claim 4.

7. An antipsychotic composition comprising as an effective ingredient the compound or salt according to claim 1.

8. An antipsychotic composition comprising as an effective ingredient the compound or salt according to claim 2.

9. An antipsychotic composition comprising as an effective ingredient the compound or salt according to claim 3.

10. An ischemic cerebral disease therapeutic composition comprising as an effective ingredient the compound or salt according to claim 1.

11. An ischemic cerebral disease therapeutic composition comprising as an effective ingredient the compound or salt according to claim 2.

12. An ischemic cerebral disease therapeutic composition comprising as an effective ingredient the compound or salt according to claim 3.

* * * * *